(12) United States Patent
Seeber et al.

(10) Patent No.: US 12,397,177 B2
(45) Date of Patent: Aug. 26, 2025

(54) TEST SYSTEM FOR TESTING A SYSTEM FOR RADIOLOGIC TREATMENT

(71) Applicant: Deutsches Krebsforschungszentrum, Heidelberg (DE)

(72) Inventors: Steffen Seeber, Heidelberg (DE); Carlos Murillo, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 231 days.

(21) Appl. No.: 18/252,555

(22) PCT Filed: Dec. 3, 2021

(86) PCT No.: PCT/EP2021/084117
§ 371 (c)(1),
(2) Date: May 11, 2023

(87) PCT Pub. No.: WO2022/117790
PCT Pub. Date: Jun. 9, 2022

(65) Prior Publication Data
US 2024/0001153 A1    Jan. 4, 2024

(30) Foreign Application Priority Data
Dec. 4, 2020    (EP) .................................... 20211971

(51) Int. Cl.
*A61N 5/10*    (2006.01)
(52) U.S. Cl.
CPC .... *A61N 5/1075* (2013.01); *A61N 2005/1076* (2013.01)
(58) Field of Classification Search
CPC .......... A61N 5/1075; A61N 2005/1076; A61B 6/583
See application file for complete search history.

(56) References Cited

U.S. PATENT DOCUMENTS

| 5,052,934 A | 10/1991 | Carey et al. |
| 7,151,253 B2 | 12/2006 | Varchena et al. |

(Continued)

FOREIGN PATENT DOCUMENTS

| EP | 2482926 B1 | 5/2014 |
| EP | 2586372 B1 | 12/2015 |

(Continued)

OTHER PUBLICATIONS

Jeroen "Development of a Soft Robotics Diaphragm to Simulate Respiratory Motion", University of Twente, MIRA CTIT, Biomedical Technology and Technical Medicine, Jul. 2019, p. 1-81. (Year: 2019).*

*Primary Examiner* — David P Porta
*Assistant Examiner* — Mamadou Faye
(74) *Attorney, Agent, or Firm* — Woodard, Emhardt, Henry, Reeves & Wagner, LLP

(57) ABSTRACT

A test system (124) for testing a system (110) for radiologic treatment. The test system (124) comprises: A • at least one anthropomorphic phantom (118) for simulating motion of at least one part of a human body (116); and B • a control device (122) for controlling the phantom (118), comprising •• a programmable logic controller (160), •• a plurality of controller nodes (162), •• a plurality of device controllers (164) configured for controlling the actuators (140), and •• at least one real-time bus interface (166) connecting the controller nodes (162) to the programmable logic controller (160) and to the device controllers (164). The programmable logic controller (160) is configured to act as a master device with respect to the controller nodes (162), specifically with respect to each of the controller nodes (162). The controller nodes (162) are configured to act as master devices with respect to the device controllers (164).

15 Claims, 3 Drawing Sheets

(56) References Cited

U.S. PATENT DOCUMENTS

| | | |
|---|---|---|
| 7,402,819 B2 | 7/2008 | Saracen |
| 7,699,522 B2 | 4/2010 | Varchena |
| 8,608,484 B2 | 12/2013 | Kalafut et al. |
| 8,681,937 B2 | 3/2014 | Garza |
| 9,965,976 B2 | 5/2018 | Tanabe et al. |
| 10,090,781 B2 | 10/2018 | Barberi et al. |
| 2005/0077459 A1 | 4/2005 | Engler et al. |
| 2010/0167251 A1 | 7/2010 | Boutchko et al. |
| 2014/0010355 A1 | 1/2014 | Seeber et al. |
| 2014/0288349 A1 | 9/2014 | Seeber et al. |
| 2018/0211740 A1 | 7/2018 | Schewiola et al. |
| 2019/0239846 A1 | 8/2019 | Sawant et al. |
| 2020/0057165 A1* | 2/2020 | Archambault ............ G01T 1/10 |

FOREIGN PATENT DOCUMENTS

| | | |
|---|---|---|
| JP | 2016101182 A | 6/2016 |
| WO | 2007064951 A2 | 6/2007 |
| WO | 2012040611 A1 | 3/2012 |
| WO | 2016148269 A1 | 9/2016 |
| WO | 2017004277 A1 | 1/2017 |
| WO | 2019197440 A1 | 10/2019 |

* cited by examiner

TEST SYSTEM FOR TESTING A SYSTEM FOR RADIOLOGIC TREATMENT

TECHNICAL FIELD

The invention relates to a test system for testing a system for radiologic treatment, to a method of simulating motion of at least one part of a human body, and to a method of testing a system for radiologic treatment. The system and methods according to the present invention specifically may be applied in the field of radiation therapy by using ionizing radiation, such as in the field of oncology. More specifically, the invention may be applied in the field of quality control and/or calibration of systems for radiologic treatment.

BACKGROUND ART

Radiation therapy by using ionizing radiation such as X-rays is a well-established method of treatment in oncology. Typically, before treatment, a radiation plan is established, including a radiation dose, a treatment schedule and a spatial region to be irradiated with ionizing radiation. In order to implement the radiation plan and in order to define a spatial region to be irradiated, many systems for radiologic treatment comprise variable multi-leaf collimators configured for shaping rays of ionizing treatment, such as described in US 2014/0288349 A1, US 2014/0010355 A1, WO 2019/197440 A1 or US 2018/0211740 A1. A major challenge in radiation therapy, however, resides in the necessity for quality control of the therapy equipment and in the necessity for assuring a compliance of the actual irradiation with the radiation plan. For this purpose, the use of phantoms resembling a human body or a part thereof is known in the art. The phantoms, as an example, may be placed on a treatment table and may be used for beam positioning, dosimetry or the like.

In the art, many types of phantoms are known. As an example, WO 2012/040611 A1 discloses anthropomorphic breast phantoms which comprise a combination of adipose tissue mimicking components and fibroglandular tissue mimicking components. Typically, x-ray attenuation coefficients or magnetic resonance relaxation times T1 and T2 are selected that are sufficiently similar to actual patient tissues. The mimicking components are distributed within the phantom such that images of the phantom contain features similar to those of patient tissues. A breast phantom can be based on a lard/egg white combination that is shaped to approximate a human breast, or a compressed human breast as prepared for mammography. The phantoms can include lesion chambers that permit the introduction of contrast agents to simulate benign or malignant lesions, and contrast agent concentration can be time varied to produce washout curves.

EP 2 586 372 B1 discloses an anthropomorphic phantom for medical imaging systems. Organ models can be fixed to corresponding plate-like second connecting elements within a hollow, torso-like humanoid housing. Lesion phantoms for simulating tumors can be fixedly secured inside each organ model using a first connecting element, which comprises a plurality of first connection holes. The distribution of those first connection holes allows to arrange the lesion phantoms at any position inside the corresponding organ model. Further, the modularized design of the anthropomorphic phantom allows to first assemble the organ models to form a module structure, and then to move the whole module structure into the humanoid housing by the use of a handle element.

U.S. Pat. No. 8,681,937 B2 discloses an apparatus and method to carry out image-guided radiotherapy or radiosurgical treatments using Kilovoltage X-ray beams. To determine the amount of the contrast agent at each point in the patient, a calibration curve is used. This calibration curve is obtained using known concentrations of the contrast agent embedded in an anthropomorphic phantom.

In some instances, phantoms simulating movements of the human body are used. As an example, U.S. Pat. No. 7,402,819 B2 discloses a respiration phantom that may be used to perform quality assurance on a radiation delivery system. The respiration phantom includes a human-like skeletal structure, at least one deformable component, and a respiration actuator. The deformable component is positionable at least partially internal to the human-like skeletal structure, has a shape resembling an organ of a human anatomy, and attenuates radiation substantially similarly to the organ of the human anatomy. The respiration actuator is positioned to deform the deformable component with a respiration-like motion.

U.S. Pat. No. 8,608,484 B2 discloses a cardiovascular flow system including a cardiovascular model system, a pump system in fluid connection with the cardiovascular model system, and an ECG simulator in communicative connection with the pump system. The ECG simulator system is adapted to create and transmit a simulated ECG signal. The ECG simulator system uses a signal received from the pump system to adjust the simulated ECG signal transmitted from the ECG simulator system. The cardiovascular flow system further includes an injection port adapted to be placed in fluid connection with an injector to inject at least one fluid into the system.

U.S. Pat. No. 5,052,934 A discloses an apparatus provided to serve as a phantom for evaluation of prosthetic valves and cardiac ultrasound procedures, wherein a controlled pulsatile flow of a blood-mimicking fluid is passed through a multi-chambered region into which are mounted mitral and aortic valves and adjustably positionable ultrasound transducers. A low friction, drive which involves very low levels of extraneous vibrational inputs, is provided with adjustment of both the volume flow rate of blood-mimicking fluid moved in each operational pulse with further control provided by relatively easily adjusted screws to selectively regulate the systolic and diastolic times of the pulsatile flow generated by a bellows arrangement. Windows made of silicone elastomer material presenting both tissue-equivalent impedance for ultrasound transmission and tissue-equivalent attenuation of the ultrasound are provided in controlled thickness to permit detailed observation of valvular flow parameters of interest, e.g., flow velocity distributions observed in the transesophogeal and apical directions. The apparatus is suitable for clinical ultrasound examination of prosthetic heart valves, the measurement of simulated blood flow velocity profiles, calibration of Doppler ultrasound parameters related to heart valve and related blood flow characteristics, and the fluid mechanical evaluation of cardiovascular devices to compare their performance for comparing competing systems.

EP 2 482 926 B1 discloses a method for checking irradiation planning in a particle therapy system. The method comprises irradiating a phantom using the control parameters stored in the irradiation planning data set and the motion signal, wherein the phantom is configured for detecting a dose distribution deposited in the phantom during or after the irradiation, wherein the phantom is a moving phantom.

WO 2017/004277 A1 discloses a dynamic phantom for use with a functional magnetic resonance imaging (fMRI) device. In one example, the dynamic phantom includes an outer housing, an inner cylinder including a removable divider, and a gearbox that can rotate the cylinder, all of which are made from fMRI-compatible materials. The divider forms longitudinal compartments inside the cylinder that can each contain a contrast material. When the cylinder contains contrast materials having at least two different concentrations, and a space between the cylinder and the housing also contains a contrast material, rotation of the cylinder produces biomimetic hemodynamic signals that may be detected by the fMRI device.

U.S. Pat. No. 7,151,253 B2 discloses a thorax phantom that enables simulation of tumor motion within a tissue equivalent material. The system consists of a tissue equivalent epoxy phantom representing a 15 cm axial section of the human thorax that includes simplified spine and lung anatomies. Within the phantom are thru rods of similar tissue density. The rods are attached to a computer-controlled actuator that facilitates both linear and rotational motion of the rods within the phantom. A plurality of tumor targets and radiation detectors can be placed within the rods at various locations thereby enabling the simulation of respiratory and cardiac induced tumor motions within the phantom and assessment of the effects of these motions on image acquisitions, treatment planning and radiation treatment delivery.

U.S. Ser. No. 10/090,781 B2 discloses a piezoelectric motor assembly for producing rotary motion. The piezoelectric motor assembly has a motor frame and a circular body rotatably mounted on the motor frame having a diameter, a thickness, and a circumferential outer surface. At least two piezoelectric motors are mounted on the motor frame in tangential engagement with the outer surface of the circular body. The at least two piezoelectric motors are biased against the outer surface, resulting in an unbalanced net force on the circular body.

U.S. Pat. No. 7,699,522 B2 discloses a quality assurance device for calibrating and testing the accuracy of movement-correlated computed tomography ("4D CT") target-locating systems. The device has a test unit sub-assembly adapted to be combined with a dynamic phantom system. The test unit sub-assembly has an axially and rotationally moveable test rod slideably disposed inside of a substantially hollow fixed housing. A matrix of markers, or "fiducials", are located in the wall of the housing. A single fiducial is located near the distal end of the moveable test rod. The distal end portion of the moveable test rod is adapted to be connected to a motion actuator, which is programmed to oscillate the test rod in a predetermined pattern. When the test unit sub-assembly is inserted into a tissue equivalent phantom member, the combined sub-assembly and phantom member can then be subjected to four-dimensional imaging to generate a visual image. A visual comparison actual relative positions of the fiducials to the know positions of the fiducials in time indicates the accuracy of the 4D CT system.

Despite the advantages achieved by the known phantoms, various technical challenges remain. Thus, firstly, patient movements still imply the risk of misalignment and, thereby, a deviation from the radiation plan during treatment. Movements of human bodies or parts thereof, however, are highly complex and involve a large number of degrees of freedom. Further, specifically in modern systems for radiologic treatment, besides the actual radiation system for generating the ionizing radiation and for irradiating the part of the human body, one or more imaging devices may be implemented which are configured for online imaging the body part during irradiation. Still, there is a need for testing the functionality of an interaction of the imaging device with the radiation system. Specifically in case an automatic adjustment of the beam shape and/or beam position is intended, a testing and a quality control of this automatic adjustment is technically challenging in view of the large number of degrees of freedom of the actual human body part. Thus, there remains a need for reliable and efficient testing means and methods which allow for a testing of systems of radiologic treatment under realistic conditions.

Problem to be Solved

It is therefore desirable to provide a test system and a method for testing a system for radiologic treatment which at least partially address the above-mentioned technical challenges. Specifically, means and methods for reliable and efficient testing shall be provided which allow for testing of radiologic treatment systems under realistic conditions.

SUMMARY

This problem is addressed by a test system for testing a system for radiologic treatment, by a method of simulating motion of at least one part of a human body, and by a method of testing a system for radiologic treatment, with the features of the independent claims. Advantageous embodiments which might be realized in an isolated fashion or in any arbitrary combinations are listed in the dependent claims as well as throughout the specification.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, a test system for testing a system for radiologic treatment is disclosed. The test system comprises:
A. at least one anthropomorphic phantom for simulating motion of at least one part of a human body, the phantom comprising
   a plurality of flexible components, each flexible component simulating at least a part of a human organ,
   a receptacle for receiving the flexible components, the receptacle being at least partially flexible, and
   a plurality of actuators configured for at least one of deforming and moving the flexible components within the receptacle; and
B. a control device for controlling the phantom, comprising
   a programmable logic controller,
   a plurality of controller nodes,
   a plurality of device controllers configured for controlling the actuators, and
   at least one real-time bus interface connecting the controller nodes to the programmable logic controller and to the device controllers.

The programmable logic controller is configured to act as a master device with respect to the controller nodes, specifically with respect to each of the controller nodes. The controller nodes are configured to act as master devices with respect to the device controllers.

The term "system" as used herein is a broad term and is to be given its ordinary and customary meaning to a person of ordinary skill in the art and is not to be limited to a special or customized meaning. The term specifically may refer, without limitation, to an arbitrary set of interacting or interdependent components or parts forming a whole. Specifically, the components may interact with each other in order to fulfill at least one common function. The at least two components may be handled independently or may be coupled or connect-able.

The term "testing" as used herein is a broad term and is to be given its ordinary and to customary meaning to a person of ordinary skill in the art and is not to be limited to a special or customized meaning. The term specifically may refer, without limitation, to a process of at least one of adjusting, obtaining and acquiring at least one item of information on at least one of a quality, a functionality and a status of an entity subject to the testing. Specifically, in the context of the testing of the system for radiologic treatment, the testing may refer to one or more of the process of quality control, e.g. by acquiring one or more items of quality information, and the process of checking the functionality or the proper functioning of one or more components of the system.

Consequently, the term "test system" as used herein also is a broad term and is to be given its ordinary and customary meaning to a person of ordinary skill in the art and is not to be limited to a special or customized meaning. The term specifically may refer, without limitation, to a system as defined above which is configured for testing at least one entity to be tested.

The term "radiologic treatment" as used herein is a broad term and is to be given its ordinary and customary meaning to a person of ordinary skill in the art and is not to be limited to a special or customized meaning. The term specifically may refer, without limitation, to the process of exposing a human patient or at least one part of a human body part to ionizing radiation, specifically at least one of X-rays, y-rays, protons and heavy ions. The exposure, specifically, may be performed for therapeutic and/or diagnostic purposes. In the following, without restricting further options, the invention will be described with reference to radiotherapy, e.g. for the purpose of oncologic treatment. As indicated, however, other options are feasible.

Consequently, the term "system for radiologic treatment" specifically may refer to a system as defined above, wherein the system is configured for radiologic treatment. Specifically, the system for radiologic treatment may comprise at least one radiation system for generating the ionizing radiation and for irradiating the at least one part of the human body with ionizing radiation. The radiation system may comprise at least one radiation source, such as an accelerator or the like. The radiation system may further comprise at least one device for one or more of controlling, adjusting and/or shaping the radiation, such as at least one collimator, e.g. a multi-leaf collimator, such as described in WO 2019/197440 A1. Further, the system for radiologic treatment may optionally also comprise at least one imaging device for imaging at least one part of the human body, such as at least one of a camera, a computer tomography device, a magnetic resonance tomography device and an ultrasound device. Other options or combinations of imaging devices are feasible.

As indicated above, the test system, firstly, comprises at least one anthropomorphic phantom for simulating motion of at least one part of a human body. The term "anthropomorphic phantom" as used herein, also simply referred to as a "phantom", is a broad term and is to be given its ordinary and customary meaning to a person of ordinary skill in the art and is not to be limited to a special or customized meaning. The term specifically may refer, without limitation, to an artificial object, which is configured to emulate physical properties of at least one part of a human body such as at least one of the shape, the density, the flexibility and the optical absorption of at least one part of a human body. The anthropomorphic phantom may respond in a similar manner to external influences such as specifically radiologic treatment as the at least one part of a human body would do, e.g. in terms of absorption of the ionizing radiation used in the radiologic treatment. The anthropomorphic phantom may comprise optically visible object structures and/or optical markers, such as for example a line grid, facilitating supervision of the anthropomorphic phantom. Additionally or alternatively, the anthropomorphic phantom, specifically in case the system for radiologic treatment comprises at least one imaging device for imaging at least one part of the human body, may also comprise at least one object and/or at least one optical marker visible by the imaging device, such as being visible in a computer tomography image and/or in a magnetic resonance tomography image.

The term "motion" as used herein is a broad term and is to be given its ordinary and customary meaning to a person of ordinary skill in the art and is not to be limited to a special or customized meaning. The term specifically may refer, without limitation, to a change of at least one of a position, an orientation and a shape of an object over time. The motion may refer to a spatial shift of the center of gravity of the object. The motion may refer to a rotation of the object. The motion may refer to a deformation of the object. The motion may refer to a superposition of at least two of a spatial shift of the center of gravity, a rotation and a deformation of the object.

The term "simulate" as used herein is a broad term and is to be given its ordinary and customary meaning to a person of ordinary skill in the art and is not to be limited to a special or customized meaning. The term specifically may refer, without limitation, to a reproduction of a process or a state of an entity by using a model process or model entity having, at least with respect to one or more parameters, identical or at least within a range of tolerance similar properties. Thus, with respect to the simulation of the motion, the simulation may provide a model process or a model entity which, with respect to one or more parameters, resembles or reproduces a motion of the at least one part of the human body, e.g. with respect to a change of at least one of shape, dimensions, position, rotation, orientation or the like.

As indicated above, the phantom, firstly, comprises a plurality of flexible components. Each flexible component is configured for simulating at least a part of a human organ. The term "flexible" as used herein is a broad term and is to be given its ordinary and customary meaning to a person of ordinary skill in the art and is not to be limited to a special or customized meaning. The term specifically may refer, without limitation, to the physical property that an object can be deformed without breaking upon application of an external force and return to its initial shape afterwards. Being flexible may comprise at least one of being bendable and being stretchable. A flexible object may comprise at least one elastic material. The term "flexible component" as used herein is a broad term and is to be given its ordinary and customary meaning to a person of ordinary skill in the art and is not to be limited to a special or customized meaning. The term specifically may refer, without limitation, to a part of the phantom as a system, the part being flexible. Thus, the flexible component may be or may comprise at least one dummy organ or a part thereof, such as an element resembling, at least in its shape, an organ of a human being or of a part thereof. The flexible component may comprise at least one housing or shell which at least partially is made of at least one flexible material. As an example, the flexible component may fully or partially be made of an elastomeric material such as silicone. For example, the flexible component may be manufactured by additive manufacturing such as printing techniques, e.g. 3D printing, e.g. 3D printing of silicone or other elastomeric materials.

The phantom further comprises at least one receptacle for receiving the flexible components. The receptacle is at least partially flexible. The term "receptacle" as used herein is a broad term and is to be given its ordinary and customary meaning to a person of ordinary skill in the art and is not to be limited to a special or customized meaning. The term specifically may refer, without limitation, to an in principle arbitrary object comprising at least one hollow interior, which can be filled with at least one further object. Thus, within the at least one interior space of the receptacle, besides the flexible components, one or more other components or media may be received. As an example, the flexible components may fully or partially be embedded in at least one matrix medium, e.g. a deformable matrix medium such as a liquid, a gel or a paste. As an example, the matrix medium may comprise agarose or other gel materials. Thus, the receptacle in the present case may comprise an outer cover, shell or artificial skin simulating the appearance of the at least one part of the human body. As an example, in case the anthropomorphic phantom is an abdominal phantom, the receptacle may comprise an outer surface which at least in parts resembles the abdominal body surface or skin in the human abdominal region.

The term "at least partially flexible" as used herein is a broad term and is to be given its ordinary and customary meaning to a person of ordinary skill in the art and is not to be limited to a special or customized meaning. The term specifically may refer, without limitation, to the physical property that at least one section or at least one part of an object is flexible, wherein the rest of the object may be non-flexible. Thus, at least a part of the receptacle may have flexible properties, such as at least a part simulating an abdominal wall of an abdominal phantom, whereas at least another part may optionally be non-flexible.

The phantom further comprises a plurality of actuators configured for at least one of deforming and moving the flexible components within the receptacle. The term "actuator" as used herein is a broad term and is to be given its ordinary and customary meaning to a person of ordinary skill in the art and is not to be limited to a special or customized meaning. The term specifically may refer, without limitation, to a device configured for exerting at least one influence onto at least one entity such as another device. The influence, as example, may be or may comprise at least one of: a mechanical influence, an electrical influence, a thermal influence, a magnetic influence, a chemical influence. Specifically, the actuator may be configured for exerting a mechanical influence onto the entity, such as at least one of a mechanical force, a pressure, an underpressure, a mechanical stress. The actuator specifically may be or may comprise at least one electromechanical actuator configured for transforming at least one electrical control signal into at least one mechanical action or influence. Specifically, as an example, the actuator may be configured for converting at least one electrical signal into at least one of a motion and a change in pressure. The actuator may comprise a single component or may comprise a plurality of interacting components. Thus, the actuator may comprise an electrical or electromechanical control part, such as an electronic control unit and/or an electrical motor, and an actuation portion, such as at least one of a movable stage, a syringe, a plunger or the like. The components of the actuator may be located in a single place or unit or may also be distributed. The latter case, as an example, may be given in pressure actuators in which, as an example, an electrical control may be separated from the syringe. Other options are feasible.

The actuators, as outlined above, may be configured for at least one of deforming and moving the flexible components located within the receptacle. For this purpose, the actuators may directly or indirectly act on the flexible components. As an example, a direct action may be exerted by the actuator being in direct contact with the flexible component. An indirect action may be exerted by the actuator exerting an influence onto at least one mediating element or entity which then exerts an influence onto the flexible organ. In both cases, which to may also be combined, an action of the actuator is transferred onto the flexible component. Further, a single actuator of the plurality of actuators may act onto one of the flexible components. Additionally or alternatively, at least one actuator of the plurality of actuators may act onto more than one of the flexible components, e.g. simultaneously. Again additionally or alternatively, a plurality of the actuators may act onto a single flexible component. Various options are feasible in order to deform and/or move the flexible components by the actuators.

As indicated above, the test system, secondly, comprises a control device for controlling the phantom. The term "control" as used herein is a broad term and is to be given its ordinary and customary meaning to a person of ordinary skill in the art and is not to be limited to a special or customized meaning. The term specifically may refer, without limitation, to an action of at least one of managing, commanding, directing and regulating a behavior of at least one further device or system, either on a defined area or on general terms within the system. In particular, this comprises collecting and/or exchanging information, preferably digital information and/or analog information, e.g. voltages and/or currents, with respect to the further device or system. In this regard, the term "control" may also comprise addressing the further device or system with jobs and/or commands. Information may comprise different system parameters that can be influenced by the further device. The term "control device" as used herein is a broad term and is to be given its ordinary and customary meaning to a person of ordinary skill in the art and is not to be limited to a special or customized meaning. The term specifically may refer, without limitation, to a device which is configured for controlling at least one further device, entity or system.

The control device, as outlined above, comprises a plurality of components, such as the programmable logic controller, the controller nodes, the device controllers the real-time bus interface. These components will be described in further detail below. It shall be noted that these components may specifically be embodied as separate components which are interconnected in order to form the control device. Alternatively, however, two or more of the components may also be fully or partially embodied as integrated components. Thus, specifically, the controller nodes and the device controllers may also be embodied as integrated components, such as by fully or partially integrating the device controllers into the controller nodes or vice versa, whereas, specifically, the remaining components of the control device as listed may be embodied as separate components.

The control device comprises a programmable logic controller. The term "programmable logic controller", which may also be abbreviated by the terms "PLC" or "SPS", as used herein is a broad term and is to be given its ordinary and customary meaning to a person of ordinary skill in the art and is not to be limited to a special or customized meaning. The term specifically may refer, without limitation, to a processor- or microprocessor-based device, specifically a processor- or microprocessor-based device configured for use in industrial environments, the device comprising a programmable memory for storing application-oriented instructions. The programmable logic controller may comprise at least one processor or processor configured for at least interpreting input signals, executing the instructions stored in the memory and determining output signals. The programmable logic controller may comprise at least one input port configured for receiving at least one input signal from at least one further device or system. The programmable logic controller may comprise at least one output port configured for sending at least one output signal to at least one further device or system. The programmable logic controller may comprise at least one serial port configured for loading at least one user program. The programmable logic controller may comprise firmware comprising invariable programs. The programmable logic controller specifically may comprise a real-time operating system configured for processing information as they come in, typically without buffer delays.

The term "processor" as used herein is a broad term and is to be given its ordinary and customary meaning to a person of ordinary skill in the art and is not to be limited to a special or customized meaning. The term specifically may refer, without limitation, to an arbitrary logic circuitry configured for performing basic operations of a computer or system, and/or, generally, to a device which is configured for performing calculations or logic operations. In particular, the processor may be configured for processing basic instructions that drive the computer or system. As an example, the processor may comprise at least one arithmetic logic unit (ALU), at least one floating-point unit (FPU), such as a math co-processor or a numeric co-processor, a plurality of registers, specifically registers configured for supplying operands to the ALU and storing results of operations, and a memory, such as an L1 and L2 cache memory. In particular, the processor may be a multi-core processor. Specifically, the processor may be or may comprise a central processing unit (CPU). Additionally or alternatively, the processor may be or may comprise a microprocessor, thus specifically the processor's elements may be contained in one single integrated circuitry (IC) chip. Additionally or alternatively, the processor may be or may comprise one or more application-specific integrated circuits (ASICs) and/or one or more field-programmable gate arrays (FPGAs) and/or one or more tensor processing unit (TPU) and/or one or more chip, such as a dedicated machine learning optimized chip, or the like. The processor specifically may be configured, such as by software programming, for performing one or more evaluation operations.

The control device further comprises a plurality of controller nodes. The term "controller node" as used herein is a broad term and is to be given its ordinary and customary meaning to a person of ordinary skill in the art and is not to be limited to a special or customized meaning. The term specifically may refer, without limitation, to a processor- or microprocessor-based device configured for distributing information within a system. The controller node may comprise at least one input port configured for receiving at least one input signal from at least one further device or system. Specifically, the controller node may receive at least one input signal from the programmable logic controller. The controller node may comprise at least one processor configured for at least one of interpreting the received information, determining at least one target device or system for the received information and manipulating the received information. The controller node may comprise at least one output port configured for forwarding the at least one input signal to the at least one target device or system. The controller node may forward the at least one input signal to at least one of the device controllers without manipulating it. The controller node may manipulate the at least one input signal and send the manipulated input signal to at least one of the device controllers.

As indicated above, the control device further comprises a plurality of device controllers configured for controlling the actuators. The term "device controller" as used herein is a broad term and is to be given its ordinary and customary meaning to a person of ordinary skill in the art and is not to be limited to a special or customized meaning. The term specifically may refer, without limitation, to a device configured for generating machine readable instructions or signals based on information received from the PLC, via at least one controller node. As an example, the device controller may comprise at least one processor configured for generating the machine readable instructions or signals which then may be transmitted to the actuators. The device controller may comprise at least one input port configured for receiving at least one input signal from at least one further device or system, such as the PLC via at least one controller node. Specifically, the device controller may receive at least one input signal from at least one of the controller nodes. The device controller may comprise at least one processor configured for transforming the input signals into output signals which are readable by at least one device such as at least one actuator. The device controller may comprise at least one compiler configured for transforming source code into machine code. The device controller may comprise at least one output port configured for sending the at least one output signal to at least one device such as at least one actuator. Specifically, the device controller may send the at least one output signal to at least one of the actuators.

The control device further comprises at least one real-time bus interface connecting the controller nodes to the programmable logic controller and to the device controllers. The term "real-time" as used herein is a broad term and is to be given its ordinary and customary meaning to a person of ordinary skill in the art and is not to be limited to a special or customized meaning. The term specifically may refer, without limitation, to a property of a system, wherein the duration of an operation within the system, e.g. at least one of an update cycle, a delay time and a response time, is predefined such as a predefined maximum duration, such as a maximum duration of 5 ms or less, or a maximum duration of 1 ms or even less. A real-time system may execute the operation within strict constraints, in particular strict time constraints referred to as deadlines. The real-time system may be said to have failed if an operation is not completed before a deadline, wherein the deadline may be set relative to an event. Typically, operation time intervals of the real-time system between an event and a system response may be in the range of Milliseconds to Microseconds. The real-time may be classified as hard real-time or soft real-time. Soft real-time may be applied in a system, when the deadlines will not be missed usually. Hard real-time may be applied in a system, when a strict time deadline is guaranteed. Missing a deadline within the hard real-time system may be classified as a total system failure. A hard real-time system may specifically ensure that all time deadlines are met.

The term "bus interface" as used herein is a broad term and is to be given its ordinary and customary meaning to a person of ordinary skill in the art and is not to be limited to a special or customized meaning. The term specifically may refer, without limitation, to a system which is configured for unidirectionally or bidirectionally exchanging information between a plurality of individual devices or systems. The bus interface may be or may comprise a serial bus interface exchanging information, e.g. one Bit, successively via one signal line. Additionally or alternatively, the bus interface may be a parallel bus interface comprising a plurality of synchronized signal lines for parallel information exchange. The bus interface may use an electrical connection and/or a connection via electromagnetic waves such as at least one of a radio frequency connection, a high-frequency connection and a photonic connection comprising optical fibers and/or optical beam paths. Further kinds of connections may be feasible.

Consequently, the term "real-time bus interface" as used herein is a broad term and is to be given its ordinary and customary meaning to a person of ordinary skill in the art and is not to be limited to a special or customized meaning. The term specifically may refer, without limitation, to a bus interface configured for real-time operation and/or for applying real-time measures.

The programmable logic controller is configured to act as a master device with respect to the controller nodes, specifically with respect to each of the controller nodes. The controller nodes are configured to act as master devices with respect to the device controllers.

The term "master device", often also referred to as a "primary device", as used herein is a broad term and is to be given its ordinary and customary meaning to a person of ordinary skill in the art and is not to be limited to a special or customized meaning. The term specifically may refer, without limitation, to a device in an asymmetric device setup, a hierarchical device setup, a asymmetric communication setup or a hierarchical communication setup which is configured for controlling or which actually controls one or more further devices or processes, often referred to as "slave devices" or "secondary devices" and in which the master device may serve as a communication hub for the one or more slave devices. The master device specifically may be or may comprise an arbitrary device configured for controlling at least one further device in connection with the master device, the further device then being referred to as slave device. The master device may be authorized to communicate via the connection between the master device and the at least one slave device without being requested, wherein the connection may specifically comprise a bus interface, more specifically a real-time bus interface. The master device may request the slave device to communicate via the connection between the master device and the slave device, also referred to as polling, wherein the connection may specifically comprise a bus interface, more specifically a real-time bus interface.

Accordingly, the term "slave device", often also referred to as a "secondary device", as used herein is a broad term and is to be given its ordinary and customary meaning to a person of ordinary skill in the art and is not to be limited to a special or customized meaning. The term specifically may refer, without limitation, to an arbitrary device configured for being controlled by at least one master device. The slave device may wait for being requested by the master device, before it communicates via the connection between the master device and the slave device, wherein the connection may specifically comprise a bus interface, more specifically a real-time bus interface. A device may simultaneously be a slave device of at least one first further device and a master device of at least one second further device different from the at least one first further device.

The programmable logic controller, as outlined above, is configured to act as a master device with respect to the controller nodes, specifically with respect to each of the controller nodes. Consequently, the controller nodes, specifically each of the controller nodes, may be configured to act as slave devices with respect to the programmable logic controller. Similarly, the device controllers, specifically each of the device controllers, may be configured to act as slave devices with respect to their corresponding controller nodes. Thus, each device controller may be assigned to at least one corresponding controller node, e.g. by software assignment and/or by hardware assignment, e.g. via the real-time bus interface. The programmable logic controller, however, may be configured for superordinate control of a functionality of the phantom. Thus, while the controller nodes may act as master devices for the corresponding device controllers, the programmable logic controller may remain superordinate master of the setup which, via the corresponding controller node, may also control the respective device controller.

The phantom may further comprise at least one sensor device. The control device may further be configured for receiving sensor data from the sensor device. The term "sensor device" as used herein is a broad term and is to be given its ordinary and customary meaning to a person of ordinary skill in the art and is not to be limited to a special or customized meaning. The term specifically may refer, without limitation, to an arbitrary device configured for at least one of detecting, measuring and monitoring at least one measurement variable and/or measurement property of at least one entity or medium. The sensor device may be configured for generating at least one signal, such as a measurement signal, e.g. an electrical signal, which is a qualitative or quantitative indicator of the measurement variable and/or measurement property. The at least one sensor device, as an example, may comprise at least one of: a voltage sensor; a resistance sensor; a current sensor; a capacitive sensor; a pressure sensor; a position sensor; a rotation sensor; a filling state sensor; a flow sensor; a gyroscopic sensor; an acceleration sensor; a velocity sensor.

The at least one sensor device may be configured for determining at least one item of state information of at least one of the flexible components. The term "item of state information" as used herein is a broad term and is to be given its ordinary and customary meaning to a person of ordinary skill in the art and is not to be limited to a special or customized meaning. The term specifically may refer, without limitation, to a qualitative and/or quantitative information, e.g. a measurement value, on a physical property of an object such as the flexible component at the present time or over a certain period of time. The item of state information may comprise at least one item selected from the group consisting of: a position of the flexible component; an orientation of the flexible component; a deformation of the flexible component; an acceleration of the flexible component; a pressure of the flexible component; flow throughput of a liquid through the flexible component; a filling level of the flexible component.

At least one of the device controllers may further be configured for controlling the at least one sensor device. Additionally or alternatively, the control device may further comprise at least one sensor device controller configured for controlling the at least one sensor device. The control device may further comprise at least one sensor controller node. The programmable logic controller may further be configured to act as a master device with respect to the at least one sensor controller node. The at least one sensor controller node may be configured to act as a master device with respect to the at least one sensor device controller. The at least one real-time bus interface may connect the at least one sensor controller node to the programmable logic controller and to the at least one sensor device controller.

The programmable logic controller may be configured for transferring at least one of the flexible components into at least one target configuration. At least one of the controller nodes may be configured for implementing the target configuration by providing commands to at least one of the device controllers. The device controller may be configured for providing at least one command corresponding to the target configuration to at least one of the actuators, the actuator being assigned to the flexible component. The term "assign" as used herein is a broad term and is to be given its ordinary and customary meaning to a person of ordinary skill in the art and is not to be limited to a special or customized meaning. The term specifically may refer, without limitation, to an allocation, specifically a non-exclusive allocation, of one entity to at least another entity. As an example, an actuator being assigned to a flexible component may act upon the flexible component and also further flexible components, wherein the flexible component may also be acted upon by further actuators. It may alternatively still be possible that an actuator being assigned to a flexible component may act upon the flexible component, only, and that beyond that no further actuators may act upon the flexible component. The assignment may be an assignment by hardwiring and/or an assignment by software.

The term "configuration" as used herein is a broad term and is to be given its ordinary and customary meaning to a person of ordinary skill in the art and is not to be limited to a special or customized meaning. The term specifically may refer, without limitation, to a physical property, e.g. at least one of a position, an orientation and a shape, of at least one object such as one of the flexible components. The configuration may refer to an arrangement and/or formation of a plurality of objects, specifically relative to each other. The term "target configuration" as used herein is a broad term and is to be given its ordinary and customary meaning to a person of ordinary skill in the art and is not to be limited to a special or customized meaning. The term specifically may refer, without limitation, to a desired configuration or nominal configuration to which the configuration is to be adjusted. The target configuration, specifically, may be or may comprise at least one of: a target position, a target orientation and a target shape. As an example, a present configuration may refer to a fillable flexible component surrounded by further flexible components, wherein the present configuration is adjusted to a desired configuration or target configuration by filling the fillable flexible component with liquid, thereby changing the shape of the fillable flexible component as well as the positions and/or shapes of the further surrounding flexible components.

The target configuration may be selected from the group consisting of a static target configuration and a dynamic target configuration. The programmable logic controller may be configured for generating the dynamic target configuration by using at least one algorithm determining a time-development of the target configuration of the flexible component. The algorithm determining the time-development of the target configuration may be configured for simulating a motion of the respective flexible component, specifically a motion of the flexible component induced by the motion of the part of the human body.

The term "algorithm" as used herein is a broad term and is to be given its ordinary and customary meaning to a person of ordinary skill in the art and is not to be limited to a special or customized meaning. The term specifically may refer, without limitation, to a finite sequence of clear and well-defined, typically computer-implementable, instructions to solve a problem or a class of problems or to perform a computation. Specifically, the algorithm may determine at least one trajectory of at least a part of the at least one flexible component. The trajectory may be determined such that the motion of the flexible component resembles the motion of at least a part of a real human body. Thus, as an example, motions of one or more organs of a human body may be simulated and/or recorded empirically or semi-empirically, in order to determine the trajectory of the at least one flexible component.

The control device may comprise at least one sensor-based feedback loop for controlling the transferring of the flexible component into the target configuration. The term "sensor-based" as used herein is a broad term and is to be given its ordinary and customary meaning to a person of ordinary skill in the art and is not to be limited to a special or customized meaning. The term specifically may refer, without limitation, to the fact that sensor data from at least one sensor may be used as information, e.g. as reference value, for subsequent decision-making processes and corresponding actions. For possible sensors and definitions thereof, reference may be made to the description above.

The term "feedback loop" as used herein is a broad term and is to be given its ordinary and customary meaning to a person of ordinary skill in the art and is not to be limited to a special or customized meaning. The term specifically may refer, without limitation, to an ongoing cycle, which occurs when outputs of a system are at least indirectly routed back as inputs to that system as part of a chain of cause-and-effect, specifically in the case that the outputs affect the next inputs which are continuously generated. As an example, the input may be the present position of a flexible component, which triggers an intended change in position of the flexible component as output, which again causes a new position of the flexible as next input.

Consequently, the term "sensor-based feedback loop" as used herein is a broad term and is to be given its ordinary and customary meaning to a person of ordinary skill in the art and is not to be limited to a special or customized meaning. The term specifically may refer, without limitation, to a feedback loop, wherein the input fed into the feedback loop is at least partially sensor-based. As an analogous example to above, the input may be the present position of a flexible component measured by at least one sensor, which triggers an intended change in position of the flexible component as output, which again causes a new position of the flexible component measured by at least one, potentially different, sensor as next input. Specifically, the programmable logic control may comprise a sensor-based feedback loop. Additionally or alternatively, at least one of the controller nodes and/or the device controllers may comprise a sensor-based feedback loop.

The test system may be configured for simulating motion of the part of the human body in a velocity range, specifically a velocity range of a velocity of movement of at least one of the flexible components, of 0 m/s to 0.20 m/s, specifically of 0 m/s to 0.10 m/s, more specifically of 0 m/s to 0.02 m/s.

The actuators, specifically independently from each other, may be selected from the group consisting of: an electromechanical actuator; a piezoelectric actuator; a hydraulic actuator; a pneumatic actuator. An electromechanical actuator may comprise at least one of a linear motor, a DC motor and a stepper motor. The actuators, specifically independently from each other, may be selected from the group consisting of: a linear motion actuator, specifically a linear motion actuator configured for at least one of pushing and pulling; a rotation actuator. A linear motion actuator may also cause a rotation motion of a flexible component.

At least one of the flexible components may comprise at least one flexible side wall and a lumen at least partially surrounded by the flexible side wall. At least one of the actuators may be assigned to the flexible component and may be configured for controlling a filling of the lumen with at least one fluidic material. The actuator may be configured for controlling at least one of a pressure of the fluidic material within the lumen and a flow of the fluidic material through the lumen. The term "lumen" as used herein is a broad term and is to be given its ordinary and customary meaning to a person of ordinary skill in the art and is not to be limited to a special or customized meaning. The term specifically may refer, without limitation, to an inner cavity of a hollow organ, e.g. the bladder, and/or tubular body structures such as intestines, arteries or veins.

The actuators may be configured for use in magnetic resonance environments. The term "magnetic resonance environment" as used herein is a broad term and is to be given its ordinary and customary meaning to a person of ordinary skill in the art and is not to be limited to a special or customized meaning. The term specifically may refer, without limitation, to a spatial area surrounding a magnetic resonance tomography device using high magnetic fields for operation. The magnetic field of the magnetic resonance tomography device may be hardly shielded in the magnetic resonance environment. The magnetic field of the magnetic resonance tomography device may not be shielded at all in the magnetic resonance environment. Thus, there may be high magnetic fields in a magnetic resonance environment. Thus, an object configured for use in magnetic resonance environments may be configured for operation in high magnetic fields. Specifically, an object configured for use in magnetic resonance environments may at least not substantially be affected by high magnetic fields. Thus, as an example, the object configured for use in magnetic resonance environments may be essentially free of ferromagnetic materials.

The test system may further comprise at least one radiation shielding for separating a treatment room from an environment. At least the programmable logic controller may be placed in the environment outside the treatment room. Further, at least one of the following components may be placed outside the treatment room: at least a part of the controller nodes; at least a part of the actuators; at least a part of the device controllers. The term "radiation shielding" as used herein is a broad term and is to be given its ordinary and customary meaning to a person of ordinary skill in the art and is not to be limited to a special or customized meaning. The term specifically may refer, without limitation, to an object configured for effectively preventing radiation, specifically ionizing radiation, from passing through it. For this purpose, the object may comprise a material with a high effective cross section with respect to the radiation, the effective cross section being a measure for an interaction between the material and the radiation such as an absorption and/or a scattering. As example, the material may be selected from the group consisting of lead, molybdenum, tungsten and uranium. Thus, the radiation shielding may comprise at least one of the shielding materials mentioned above. Additionally, the radiation shielding may also be configured for effectively preventing electromagnetic fields, specifically magnetic fields, from passing through it. For this purpose, the object may comprise a material which can easily be magnetized such as iron.

The term "treatment room" as used herein is a broad term and is to be given its ordinary and customary meaning to a person of ordinary skill in the art and is not to be limited to a special or customized meaning. The term specifically may refer, without limitation, to a room for medical treatment, specifically for radiologic treatment, more specifically for diagnostic radiologic treatment, but optionally also for therapeutic radiologic treatment. Specifically, the treatment room may refer to a room in which a magnetic resonance tomography device is located. Thus, the treatment room may comprise a magnetic resonance environment. The treatment room may further comprise at least one radiation shielding. Specifically, at least one wall of the treatment room may comprise at least one radiation shielding. As indicated above, a distributed allocation of the control device may allow locating rather radiation-sensitive devices of the control device outside the treatment room while locating rather radiation-insensitive devices of the control device inside the treatment room.

The control device may further comprise a system clock. The programmable logic controller may be configured to communicate with the controller nodes and the controller nodes may be configured to communicate with the device controllers in predefined time intervals defined by the system clock. The predefined time intervals may have a length of 0.1 Milliseconds to 100 Milliseconds, specifically 1 Millisecond to 10 Milliseconds, more specifically 1 Millisecond. The term "system clock" as used herein is a broad term and is to be given its ordinary and customary meaning to a person of ordinary skill in the art and is not to be limited to a special or customized meaning. The term specifically may refer, without limitation, to a clock and/or a device, which may be able to provide a clock pulse and/or a beat, specifically a periodic signal, specifically with high accuracy and periodicity. In particular, the system clock may be triggering and/or synchronizing an update cycle. Herein, the system clock may comprise and/or be connected to at least one electronic trigger and/or at least one crystal oscillator and/or at least one atomic clock. The electronic trigger and/or the crystal oscillator and/or the atomic clock may be implemented in the control device or may be provided by an external device, e.g. by broadcasting a signal, e.g. by using at least one cable and/or a radio frequency signal. Thus, the clock pulse and/or the beat and/or the system clock may be generated in the control device or may be generated, e.g. by an atomic clock outside the control device. Inside the control device, the clock pulse and/or the beat and/or the system clock may be provided by a crystal oscillator, specifically a crystal oscillator which may be able to create an electrical signal, e.g. the beat, with a very precise frequency, e.g. for providing beats with frequencies from about 1 kHz to 100 MHz, specifically from 1 MHz to 50 MHz.

The control device may be configured for executing a real-time protocol, wherein an exchange of a command between the programmable logic controller and the controller nodes and an exchange of a command between at least one of the controller nodes and at least one of the device controllers may take place within one predefined time interval. When executing the real-time protocol, the exchange of a command between the programmable logic controller and the controller nodes and between at least one of the controller nodes and at least one of the device controllers may be bidirectional. As an example, within one predefined time interval the programmable logic controller may send a target configuration for at least one flexible component via at least one controller node to at least one device controller and still within the same predefined time interval the programmable logic controller may receive back information about the actual configuration from at least one of the device controllers via at least one of the controller nodes.

A cycle rate of the control device may be 0.5 kHz to 20 kHz, specifically 1 kHz to 8 kHz. The real-time bus interface may comprise at least one hard real-time field bus interface, specifically at least one of: a field-bus, specifically an Ethernet-based fieldbus; an EtherCAT, a DeviceNet, a Profibus, a Profinet, an Interbus, a Modbus and a SERCOS. The programmable logic controller may be a device according to the DIN/EN IEC 61131 standard and/or the IEC 61131 standard, specifically IEC 61131-3. The programmable logic controller may comprise at least one feedback loop, such as a feedback loop comprising a proportional-integral-derivative controller.

The phantom may be configured for simulating motion of at least an abdominal section of the human body. The human body may be a male human body. The flexible components may comprise at least one flexible component selected from the group consisting of: a flexible component simulating a human bladder; a flexible component simulating a human intestine; a flexible component simulating a human rectum; a flexible component simulating a human prostate. The test system may be configured for controlling filling of the flexible components simulating an action of one of a human bladder and a human rectum.

At least one of the actuators may be operatively connected to at least one membrane, specifically at least one synthetic membrane. The actuator operatively connected to the membrane may be configured for simulating at least one motion of the human body, selected from the group consisting of: a breathing; a swallowing; a coughing; a hiccup. The membrane may comprise a synthetic diaphragm.

The term "operatively connected" as used herein is a broad term and is to be given its ordinary and customary meaning to a person of ordinary skill in the art and is not to be limited to a special or customized meaning. The term specifically may refer, without limitation, to a configuration of at least two components in which at least a first one of the components may directly or indirectly act on at least a second one of the components. Specifically, the actuator may be configured for controlling at least one motion of the membrane. The actuator being operatively connected to the membrane may be configured for acting upon the membrane, e.g. to pull on at least a part of the membrane and/or to press at least a part of the membrane. For this purpose, the actuator may touch the membrane at least temporarily, but not necessarily constantly. The actuator may be operatively connected to the membrane exclusively or the actuator may be operatively connected to at least one further entity and/or at least one further actuator may be operatively connected to the membrane.

The term "membrane" as used herein is a broad term and is to be given its ordinary and customary meaning to a person of ordinary skill in the art and is not to be limited to a special or customized meaning. The term specifically may refer, without limitation, to at least one layer, specifically a flexible layer, configured for separating and/or covering objects such as organs, wherein the layer may be selectively permeable for material transport through it. The membrane may comprise at least one biological material from a human body and/or an animal body. The term "synthetic" as used herein is a broad term and is to be given its ordinary and customary meaning to a person of ordinary skill in the art and is not to be limited to a special or customized meaning. The term specifically may refer, without limitation, to an entity not originating from nature, wherein the entity may comprise an artificially produced object, wherein the artificially produced object may specifically comprise a chemically synthesized material. As an example, a synthetic entity may comprise a plastic form and/or a plastic layer. Consequently, the term "synthetic membrane" as used herein is a broad term and is to be given its ordinary and customary meaning to a person of ordinary skill in the art and is not to be limited to a special or customized meaning. The term specifically may refer, without limitation, to a membrane comprising synthetic components.

The anthropomorphic phantom, specifically at least one of the flexible components, may comprise at least one cavity for receiving at least one dosimeter. The dosimeter which may be a part of the anthropomorphic phantom or which may be a separate component may be a device configured for generating at least one item of information on a dose of ionizing radiation by which the anthropomorphic phantom and/or the dosimeter is exposed. As an example, the cavity may be accessible from an outer environment of the phantom, e.g. for introducing and/or removing the dosimeter.

In a second aspect, a method of simulating motion of at least one part of a human body is disclosed. The method of simulating motion of at least one part of a human body comprises the following method steps:
  i. providing at least one test system as described herein, e.g. according to any one of the embodiments disclosed above and/or according to any one the embodiments disclosed in further detail below;

ii. transferring, by using the programmable logic controller, at least one of the flexible components into at least one target configuration, wherein at least one of the controller nodes implements the target configuration by providing commands to at least one of the device controllers, wherein the device controller provides at least one command corresponding to the target configuration to at least one of the actuators, the actuator being assigned to the flexible component.

At least step ii. may be computer-controlled. Further, one or more of the method steps may be performed once or repeatedly. The method may comprise further method steps which are not listed.

In a third aspect, a method of testing a system for radiologic treatment is disclosed. The system comprises at least one imaging device for imaging at least one part of a human body. The system further comprises least one radiation system for irradiating the part of the human body with ionizing radiation. The system is configured for controlling the irradiation in accordance with at least one item of information on a spatial configuration of the part of the human body.

The term "imaging device" as used herein is a broad term and is to be given its ordinary and customary meaning to a person of ordinary skill in the art and is not to be limited to a special or customized meaning. The term specifically may refer, without limitation, to a device configured for generating at least one visual representation of at least one object, specifically of an interior of a human body, specifically for medical analysis. Thus, the imaging device may be configured for generating visual representations of the functioning of at least one organ of the human body. The imaging device may be selected from the group consisting of: a photo camera, a thermographic camera, an endoscope, an ultrasound device, a magnetic resonance tomography device, a computer tomography device.

The term "item of information" as used herein is a broad term and is to be given its ordinary and customary meaning to a person of ordinary skill in the art and is not to be limited to a special or customized meaning. The term specifically may refer, without limitation, to at least one of data, knowledge or evidence providing a qualitative and/or quantitative description of at least one entity, such as on a physical property of an object. Specifically, the item of information may comprise at least one image of at least one part of the human body at a present time and/or a video sequence showing at least one part of the human body over a certain period of time. Additionally or alternatively, the at least one item of information may be or may comprise at least one item of spatial information derived from the at least one image, such as at least one of a position, an orientation and a shape of at least one organ and/or a part thereof.

The method of testing a system for radiologic treatment comprises the following method steps:
I. providing at least one test system according to any one of the embodiments disclosed above referring to a test system and/or according to any one of the embodiments referring to a test system disclosed in further detail below;
II. placing the phantom of the test system into at least one treatment position of the system for radiologic treatment;
III. imaging at least one part of the phantom by using the imaging device of the system for radiologic treatment;
IV. simulating motion of at least one part of a human body by using the method according to any one of the method embodiments disclosed above and/or according to any one of the embodiments referring to a method of simulating motion of at least one part of a human body disclosed in further detail below;
V. evaluating a system response of the system for radiologic treatment to the simulated motion.

The method steps may be performed in the given order. It shall be noted, however, that a different order is also possible. Further, one or more of the method steps may be performed once or repeatedly. Further, two or more of the method steps may be performed simultaneously or in a timely overlapping fashion. The method may comprise further method steps which are not listed.

The term "treatment position" as used herein is a broad term and is to be given its ordinary and customary meaning to a person of ordinary skill in the art and is not to be limited to a special or customized meaning. The term specifically may refer, without limitation, to a position suitable for medical treatment, specifically radiologic treatment. As an example, the treatment position may be or may comprise at least one position defined by at least one patient positioning system, such as a patient positioning system selected from the group consisting of a bed, a backrest and a stool. Thus, the imaging device and/or the radiation system may be aligned with respect to the treatment position. Further, the treatment position may be directly accessible by the imaging device and/or the radiation system. As an example, the treatment position might be in a tube comprised by a magnetic resonance tomography device and/or a computer tomography device.

The term "evaluating" as used herein is a broad term and is to be given its ordinary and customary meaning to a person of ordinary skill in the art and is not to be limited to a special or customized meaning. The term specifically may refer, without limitation, to a processing of at least one item of input information, in order to generate at least one item of result information. Specifically, the term may refer to the process of computing and/or determining at least one result with a corresponding output, e.g. a prospective measure, based on input data such as parameters describing a present state. Specifically, the evaluating may define an adaption of a system to a change in a present state. The term "system response" as used herein is a broad term and is to be given its ordinary and customary meaning to a person of ordinary skill in the art and is not to be limited to a special or customized meaning. The term specifically may refer, without limitation, to measures undertaken by a system in reaction to a change in a present state. As an example, the imaging device and/or the radiation system of the system for radiologic treatment may be aligned on the position of a flexible component of the phantom, but upon observation of a change in position of the flexible component, a re-alignment to the new position of the flexible component may be initiated. Alternatively, the phantom as whole may be moved automatically to bring the flexible component back to its initial position without changing the alignment of the imaging device and/or the radiation system.

The evaluation of the system response in step V. may comprise evaluating if the controlling of the irradiation in accordance with the at least one item of information on the spatial configuration of the part of the human body comprises recognizing a re-configuration due to the motion simulated in step IV. Thus, as an example, by using the simulated motion in step IV., the movement of at least a part of the human body may be simulated, and the method of testing the system for radiologic treatment may, in step V., determine if the system recognizes the motion and, optionally, takes appropriate action, such as by re-adjusting the irradiation, generating a warning, stopping the irradiation or the like. Thus, the system may be configured for recognizing a motion of the human body or a part thereof and may take appropriate action. By the method of testing a system, information may be generated on a proper functioning of this recognition and/or the correctness of the action.

Thus, the evaluation of the system response in step V. may further comprise adjusting the irradiation in accordance with the recognized re-configuration, specifically by at least one of adjusting a spatial configuration of the irradiation, adjusting an orientation of the irradiation and adjusting a shape of the irradiation. The irradiation may be paused during the adjusting. The term "shape of the irradiation" as used herein is a broad term and is to be given its ordinary and customary meaning to a person of ordinary skill in the art and is not to be limited to a special or customized meaning. The term specifically may refer, without limitation, to a geometric shape, e.g. a diameter, of at least one ray. A collimator may be used for shaping rays such as described in WO 2019/197440 A1.

The method of testing a system for radiologic treatment may further comprise providing information on the evaluating in step V., specifically by providing an evaluation report. The term "providing" as used herein is a broad term and is to be given its ordinary and customary meaning to a person of ordinary skill in the art and is not to be limited to a special or customized meaning. The term specifically may refer, without limitation, to the process of making something available to a person or an entity. Thus, the evaluation report may comprise a documentation of at least one evaluation and a giving out the documentation, e.g. in form of a report comprising a starting point of the evaluation and an outcome of the evaluation. The evaluation report may be made available by at least one of: displaying the evaluation report, e.g. by at least one of a visual output, an audible output and a haptic output; storing the evaluation report, e.g. in at least one data storage device; transmitting the evaluation report, e.g. via at least one wireless and/or at least one wire-bound interface, e.g. to another device. As an example, a report may be given out, the report comprising a development of a position of one of the flexible components of the phantom at the points in time when a motion of the phantom is simulated, the report further comprising a corresponding re-alignment of the imaging device and/or the radiation system and/or the phantom as whole.

The methods as described herein, such as according to any one of the embodiments discussed above and/or according to any one of the embodiments shown in further detail below, may at least partially be computer-implemented or computer-controlled. Thus, at least step ii. of the method of simulating motion of at least one part of a human body may be computer-implemented or computer-controlled. Similarly, at least steps III. to V. of the method of testing the system for radiologic treatment may be computer-controlled. Consequently, further disclosed is a computer program including computer-executable instructions for performing at least step ii. of method of simulating motion of at least one part of a human body, when executed by a computer, specifically by the control device of the test system as disclosed herein. Further, a computer program including computer-executable instructions for performing at least steps III. to V. of the method of testing the system for radiologic treatment, when executed by a computer, specifically by the control device of the test system as disclosed herein, is disclosed. Further disclosed are computer-readable data carriers and/or computer-readable storage media having a data structure stored thereon, which, after loading into a computer or computer network, specifically the control device of the test system as disclosed herein, may execute at least step ii. of method of simulating motion of at least one part of a human body or at least steps III. to V. of the method of testing the system for radiologic treatment, when executed by a computer, specifically by the control device of the test system as disclosed herein. As used herein, the terms "computer-readable data carrier" and "computer-readable storage medium" specifically may refer to non-transitory data storage means, such as a hardware storage medium having stored thereon computer-executable instructions. The computer-readable data carrier or storage medium specifically may be or may comprise a storage medium such as a random-access memory (RAM) and/or a read-only memory (ROM).

The test system and methods according to the present invention may provide a large number of advantages over known methods, stations and systems. In particular, they allow for a more effective testing of in principle all kinds of systems for radiologic treatment such as magnetic resonance tomography devices, computer tomography devices or radiation systems. They are specifically also suitable for new hybrid devices such as an MR-Linac. Furthermore, they allow for a more effective testing of algorithms simulating a motion or a deformation of organs. With the test system and methods according to the present invention organ-specific complex three dimensional movements and deformations can be simulated more realistically, deterministically and reproducibly in real-time. In particular, the interconnected movements and deformations of entire organ-assemblies comprising several organs can be simulated more realistically, deterministically and reproducibly in real-time—specifically in the context of a filling of the rectum or the bladder. Results can be used in therapy planning systems for realizing fast situation-specific adjustments in response to an organ movement or deformation. Thereby, the risk of unintentionally damaging healthy tissue of a patient can be reduced during future radiologic treatments. Consequently, smaller safety regions during treatment can be sufficient preserving the patient's health. Thus, monitoring of an entire treatment chain including the patient positioning before and during a treatment can be improved. Further, monitoring of adaptive therapy methods such as for instance gating can be improved as well as tumor-tracing during treatment. Moreover, due to the distributed allocation of the control device radiation-sensitive parts of the control device can be positioned outside the treatment room to achieve less interference in imaging. Consequently, higher field strengths can also be used inside the treatment room during radiologic treatment. Further, maintenance of the system is also facilitated, since within the treatment room components can be used which are easily replaceable after being damaged through high field strengths. At the same time, most computing power can be positioned safely and easily accessible outside the treatment room.

Thus, by using the test system and/or any one of the methods according to the present invention, a process chain of radio therapy may be subject to quality control, without the necessity of a patient being exposed to the process. Specifically a correct patient positioning before and during treatment may be checked and subject to quality control. Additionally or alternatively, adaptive methods of radio therapy may be checked and simulated, such as gating techniques. Additionally or alternatively, a tumor tracing during exposure may be subject to checking and quality control, such as by simulating motion of a tumor by using the anthropomorphic phantom and checking if the system correctly reacts to the motion, e.g. by correctly re-adjusting a multi leaf collimator or other components. Additionally or alternatively, a functioning of the imaging device may be subject to quality control, such as by checking if the imaging device and/or an image recognition algorithm running on the system correctly recognizes positional changes. Additionally or alternatively, a quality control of a re-planning algorithm of the system may be subject to quality control, such as by checking if a real-time re-planning of exposure parameters by the system is performed correctly. Generally, a quality control of any system response of the system may be performed by using the test system, such as a system response to positional changes, e.g. a system response including re-planning of a treatment plan or radiation plan in response to positional changes. Thereby, improving the quality control by using the test system and/or the methods according to the present invention, a detrimental exposure of the patient in any subsequent treatment process using the system may be reduced. Specifically, by improving the quality control process, safety regions around the tumor in the therapy plan may finally be reduced, leading to a reduced exposure of healthy tissue and, thus, to a more careful or gentle treatment.

Summarizing and without excluding further possible embodiments, the following embodiments may be envisaged:

Embodiment 1: A test system for testing a system for radiologic treatment, comprising
  A. at least one anthropomorphic phantom for simulating motion of at least one part of a human body, the phantom comprising
  a plurality of flexible components, each flexible component simulating at least a part of a human organ,
  a receptacle for receiving the flexible components, the receptacle being at least partially flexible, and
  a plurality of actuators configured for at least one of deforming and moving the flexible components within the receptacle; and
  B. a control device for controlling the phantom, comprising
  a programmable logic controller,
  a plurality of controller nodes,
  a plurality of device controllers configured for controlling the actuators, and
  at least one real-time bus interface connecting the controller nodes to the programmable logic controller and to the device controllers,
  wherein the programmable logic controller is configured to act as a master device with respect to the controller nodes, specifically with respect to each of the controller nodes, wherein the controller nodes are configured to act as master devices with respect to the device controllers.

Embodiment 2: The test system according to the preceding embodiment, wherein the controller nodes, specifically each of the controller nodes, are configured to act as slave devices with respect to the programmable logic controller.

Embodiment 3: The test system according to any one of the preceding embodiments, wherein the device controllers, specifically each of the device controllers, are configured to act as slave devices with respect to their corresponding controller nodes.

Embodiment 4: The test system according to any one of the preceding embodiments, wherein the programmable logic controller is configured for superordinate control of a functionality of the phantom.

Embodiment 5: The test system according to any one of the preceding embodiments, wherein the phantom further comprises at least one sensor device, wherein the control device is further configured for receiving sensor data from the sensor device.

Embodiment 6: The test system according to the preceding embodiment, wherein the at least one sensor device is configured for determining at least one item of state information of at least one of the flexible components.

Embodiment 7: The test system according to the preceding embodiment, wherein the item of state information comprises at least one item selected from the group consisting of: a position of the flexible component; an orientation of the flexible component; a deformation of the flexible component; an acceleration of the flexible component; a pressure of the flexible component; flow throughput of a liquid through the flexible component; a filling level of the flexible component.

Embodiment 8: The test system according to any one of the three preceding embodiments, wherein at least one of the device controllers is further configured for controlling the at least one sensor device.

Embodiment 9: The test system according to any one of the four preceding embodiments, wherein the control device further comprises at least one sensor device controller configured for controlling the at least one sensor device, wherein the control device further comprises at least one sensor controller node, wherein the programmable logic controller is further configured to act as a master device with respect to the at least one sensor controller node, wherein the at least one sensor controller node is configured to act as a master device with respect to the at least one sensor device controller, wherein the at least one real-time bus interface connects the at least one sensor controller node to the programmable logic controller and to the at least one sensor device controller.

Embodiment 10: The test system according to any one of the preceding embodiments, wherein the programmable logic controller is configured for transferring at least one of the flexible components into at least one target configuration, wherein at least one of the controller nodes is configured for implementing the target configuration by providing commands to at least one of the device controllers, wherein the device controller is configured for providing at least one command corresponding to the target configuration to at least one of the actuators, the actuator being assigned to the flexible component.

Embodiment 11: The test system according to the preceding embodiment, wherein the target configuration is selected from the group consisting of a static target configuration and a dynamic target configuration.

Embodiment 12: The test system according to the preceding embodiment, wherein the programmable logic controller is configured for generating the dynamic target configuration by using at least one algorithm determining a time-development of the target configuration of the flexible component.

Embodiment 13: The test system according to the preceding embodiment, wherein the algorithm determining the time-development of the target configuration is configured for simulating a motion of the respective flexible component, specifically a motion of the flexible component induced by the motion of the part of the human body.

Embodiment 14: The test system according to any one of the four preceding embodiments, wherein the control device comprises at least one sensor-based feedback loop for controlling the transferring of the flexible component into the target configuration.

Embodiment 15: The test system according to any one of the preceding embodiments, wherein the test system is configured for simulating motion of the part of the human body in a velocity range, specifically a velocity range of a velocity of movement of at least one of the flexible components, of 0 m/s to 0.20 m/s, specifically of 0 m/s to 0.10 m/s, more specifically of 0 m/s to 0.02 m/s.

Embodiment 16: The test system according to any one of the preceding embodiments, wherein the actuators, specifically independently from each other, are selected from the group consisting of: an electromechanical actuator; a piezoelectric actuator; a hydraulic actuator; a pneumatic actuator.

Embodiment 17: The test system according to any one of the preceding embodiments, wherein the actuators, specifically independently from each other, are selected from the group consisting of: a linear motion actuator, specifically a linear motion actuator configured for at least one of pushing and pulling; a rotation actuator.

Embodiment 18: The test system according to any one of the preceding embodiments, wherein at least one of the flexible components comprises at least one flexible side wall and a lumen at least partially surrounded by the flexible side wall, wherein at least one of the actuators is assigned to the flexible component and is configured for controlling a filling of the lumen with at least one fluidic material.

Embodiment 19: The test system according to the preceding embodiment, wherein the actuator is configured for controlling at least one of a pressure of the fluidic material within the lumen and a flow of the fluidic material through the lumen.

Embodiment 20: The test system according to any one of the preceding embodiments, wherein the actuators are configured for use in magnetic resonance environments.

Embodiment 21: The test system according to any one of the preceding embodiments, further comprising at least one radiation shielding for separating a treatment room from an environment, wherein at least the programmable logic controller is placed in the environment outside the treatment room.

Embodiment 22: The test system according to the preceding embodiment, wherein, wherein, further, at least one of the following components is placed outside the treatment room: at least a part of the controller nodes; at least a part of the actuators; at least a part of the device controllers.

Embodiment 23: The test system according to any one of the preceding embodiments, wherein the control device further comprises a system clock, wherein the programmable logic controller is configured to communicate with the controller nodes and wherein the controller nodes are configured to communicate with the device controllers in predefined time intervals defined by the system clock.

Embodiment 24: The test system according to the preceding embodiment, wherein the predefined time intervals have a length of 0.1 Milliseconds to 100 Milliseconds, specifically 1 Millisecond to 10 Milliseconds, more specifically 1 Millisecond.

Embodiment 25: The test system according to any one of the two preceding embodiments, wherein the control device is configured for executing a real-time protocol, wherein an exchange of a command between the programmable logic controller and the controller nodes and an exchange of a command between at least one of the controller nodes and at least one of the device controllers takes place within one predefined time interval.

Embodiment 26: The test system according to any one of the preceding embodiments, wherein a cycle rate of the control device is 0.5 kHz to 20 kHz, specifically 1 kHz to 8 kHz.

Embodiment 27: The test system according to any one of the preceding embodiments, wherein the real-time bus interface comprises at least one hard real-time field bus interface, specifically at least one of: field-bus, specifically an Ethernet-based fieldbus; an EtherCAT, a DeviceNet, a Profibus, a Profinet, an Interbus, a Modbus and a SERCOS.

Embodiment 28: The test system according to any one of the preceding embodiments, wherein the programmable logic controller is a device according to the DIN/EN IEC 61131 standard and/or the IEC 61131 standard, specifically IEC 61131-3.

Embodiment 29: The test system according to any one of the preceding embodiments, wherein the programmable logic controller comprises at least one feedback loop, specifically a proportional-integral-derivative controller.

Embodiment 30: The test system according to any one of the preceding embodiments, wherein the phantom is configured for simulating motion of at least an abdominal section of the human body.

Embodiment 31: The test system according to the preceding embodiment, wherein the human body is a male human body.

Embodiment 32: The test system according to any one of the preceding embodiments, wherein the flexible components comprise at least one flexible component selected from the group consisting of: a flexible component simulating a human bladder; a flexible component simulating a human intestine; a flexible component simulating a human rectum; a flexible component simulating a human prostate.

Embodiment 33: The test system according to the preceding embodiment, wherein the test system is configured for controlling filling of the flexible components simulating an action of one of a human bladder and a human rectum.

Embodiment 34: The test system according to any one of the preceding embodiments, wherein at least one of the actuators is operatively connected to at least one membrane, specifically at least one synthetic membrane.

Embodiment 35: The test system according to the preceding embodiment, wherein the actuator operatively connected to the membrane is configured for simulating at least one motion of the human body, selected from the group consisting of: a breathing; a swallowing; a coughing; a hiccup.

Embodiment 36: The test system according to any one of the two preceding embodiments, wherein the membrane comprises a synthetic diaphragm.

Embodiment 37: The test system according to any one of the preceding embodiments, wherein the phantom, specifically at least one of the flexible components, comprises at least one cavity for receiving at least one dosimeter.

Embodiment 38: A method of simulating motion of at least one part of a human body, the method comprising:
i. providing at least one test system according to any one of the preceding embodiments;
ii. transferring, by using the programmable logic controller, at least one of the flexible components into at least one target configuration, wherein at least one of the controller nodes implements the target configuration by providing commands to at least one of the device controllers, wherein the device controller provides at least one command corresponding to the target configuration to at least one of the actuators, the actuator being assigned to the flexible component.

Embodiment 39: The method according to the preceding embodiment, wherein at least step ii. is computer-controlled.

Embodiment 40: A method of testing a system for radiologic treatment, the system comprising at least one imaging device for imaging at least one part of a human body and at least one radiation system for irradiating the part of the human body with ionizing radiation, the system being configured for controlling the irradiation in accordance with at least one item of information on a spatial configuration of the part of the human body, the method comprising:
I. providing at least one test system according to any one of the preceding embodiments referring to a test system;
II. placing the phantom of the test system into at least one treatment position of the system for radiologic treatment;
III. imaging at least one part of the phantom by using the imaging device of the system for radiologic treatment;
IV. simulating motion of the phantom by using the method according to any one of the preceding method embodiments;
V. evaluating a system response of the system for radiologic treatment to the simulated motion.

Embodiment 41: The method according to the preceding embodiment, wherein the evaluation of the system response in step V. comprises evaluating if the controlling of the irradiation in accordance with the at least one item of information on the spatial configuration of the part of the human body comprises recognizing a re-configuration due to the motion simulated in step IV. and further comprises adjusting the irradiation in accordance with the recognized re-configuration, specifically by at least one of adjusting a spatial configuration of the irradiation, adjusting an orientation of the irradiation and adjusting a shape of the irradiation.

Embodiment 42: The method according to the preceding embodiment, wherein the irradiation is paused during the adjusting.

Embodiment 43: The method according to any one of the three preceding embodiments, wherein the method further comprises providing information on the evaluating in step V., specifically by providing an evaluation report.

Embodiment 44: The method according to any one of the four preceding embodiments, wherein at least steps III. to V. are computer-controlled.

SHORT DESCRIPTION OF THE FIGURES

Further optional features and embodiments will be disclosed in more detail in the subsequent description of embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

DETAILED DESCRIPTION OF THE EMBODIMENTS

Figure 1:
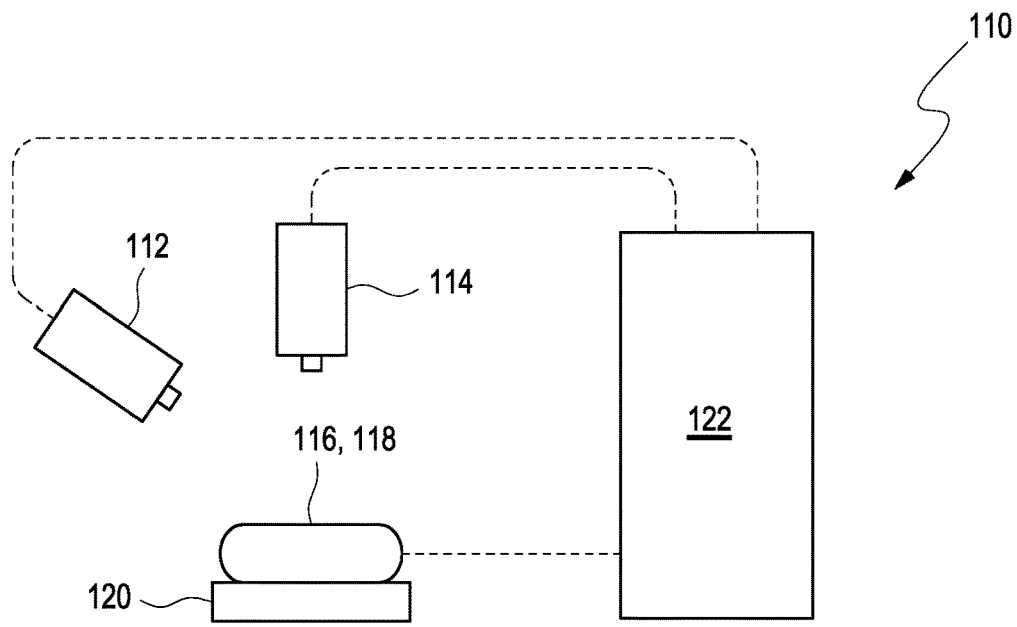
FIG. 1 shows a schematic view of an exemplary system for radiologic treatment.

In FIG. 1, a schematic view of an exemplary embodiment of a system 110 for radiologic treatment is disclosed. The system 110 comprises at least one imaging device 112 for imaging at least one part of a human body and at least one radiation system 114 for irradiating the part of the human body with ionizing radiation.

In FIG. 1, the at least one part of the human body is denoted by reference number 116. The part of the human body 116 may, for testing purposes and/or calibration purposes, as described below, be replaced by at least one anthropomorphic phantom 118, which is also symbolically depicted in FIG. 1. The part of the human body 116 and/or the anthropomorphic phantom 118 may rest on a bed 120 or any other type of patient positioning system.

The system 110 for radiologic treatment may further comprise at least one control device 122 which, as an example, is connected to the radiation system 114 and is configured for controlling at least the radiation system 114. The control device 122 may further be connected to the imaging device 112 and may also be configured for controlling imaging the at least one part of the human body 116 and/or the anthropomorphic phantom 118. The control device 122 may, as an example, comprise at least one processor and may optionally be configured for controlling the irradiation of the part of the human body 116 and/or the anthropomorphic phantom 118 in accordance with the at least one item of information on a spatial configuration of the part of the human body 116 and/or the anthropomorphic phantom 118, as gathered by the imaging device 112. Thus, as an example, the control device 122 may recognize a re-configuration due to the motion of the part of the human body 116 and/or the anthropomorphic phantom 118 and adjust the irradiation in accordance with the recognized re-configuration, specifically by at least one of adjusting a spatial configuration of the irradiation, adjusting an orientation of the irradiation and adjusting a shape of the irradiation.

Figure 2:
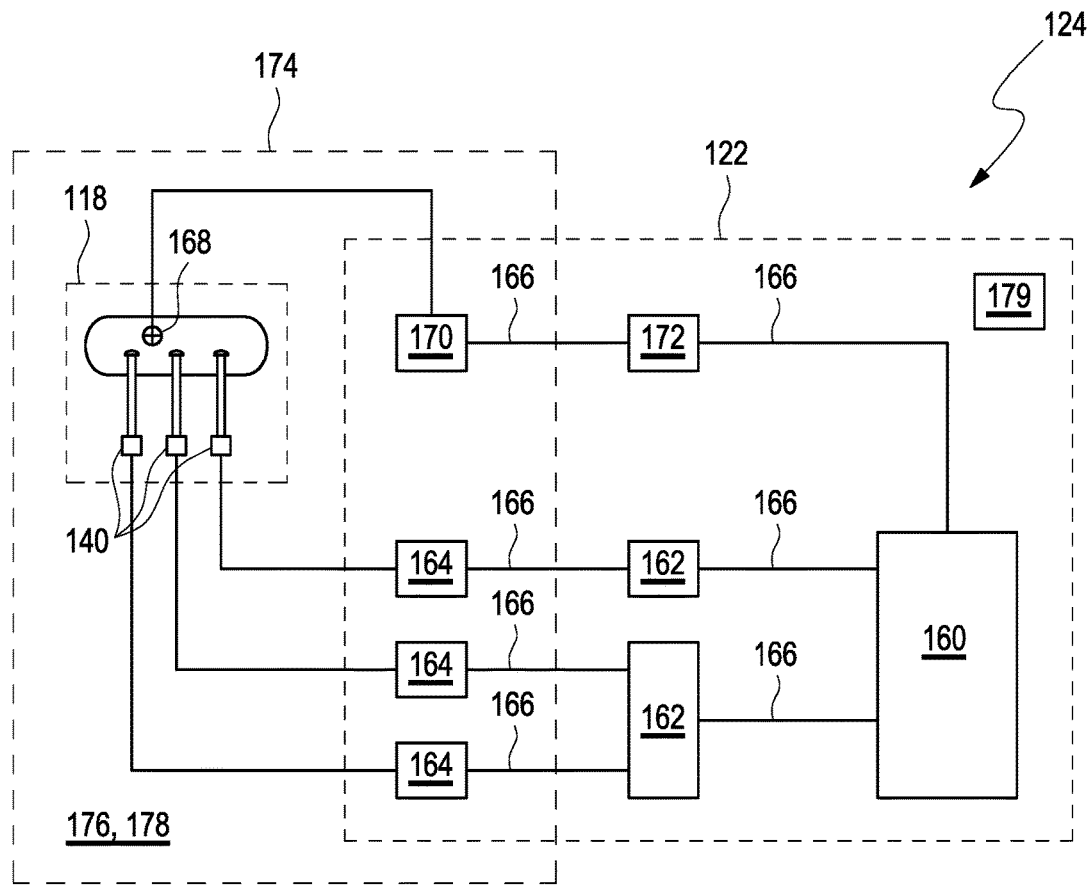
FIG. 2 shows a schematic view of an embodiment of a test system for testing a system for radiologic treatment.

In FIG. 2, a schematic view of a test system 124 is shown. The test system 124 is configured for testing a system for radiologic treatment, such as the system 110 as depicted in FIG. 1.

The test system 124 as depicted in FIG. 2, comprises at least one anthropomorphic phantom 118. As outlined above, the anthropomorphic phantom 118 may be used in the system 110 for radiologic treatment in FIG. 1, e.g. for simulating the part of the human body 116 and/or for quality control or calibration purposes. In the context of the present invention, the anthropomorphic phantom 118 is configured for simulating motion of the at least one part of the human body 116. Thus, the anthropomorphic phantom 118, as will be outlined in further detail below, may be controlled in order to simulate the motion of the at least one part of the human body 116.

Figure 3:
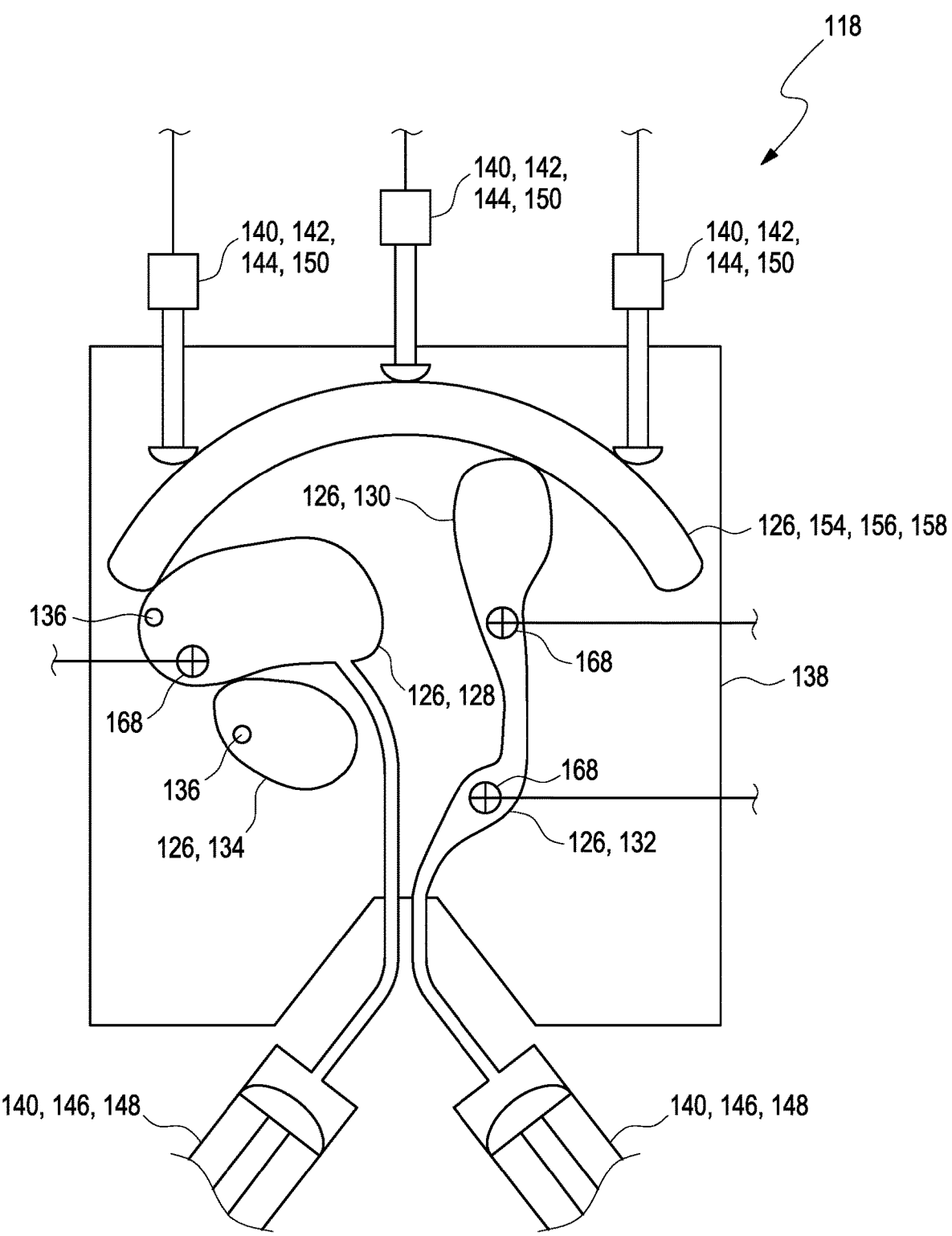
FIG. 3 shows a schematic view of an embodiment of an anthropomorphic phantom according to the invention.

An exemplary embodiment of an anthropomorphic phantom 118 which may be used in the test system 124 of FIG. 2 is depicted symbolically in FIG. 3. In the following, FIGS. 2 and 3 will be described in conjunction.

As can be seen in FIG. 3, the anthropomorphic phantom 118 comprises a plurality of flexible components 126. Each flexible component 126 is configured for simulating at least a part of a human organ. The flexible components 126 may be or may comprise dummy or phantom organs which, as will be outlined in further detail below, may be controlled, e.g. by controlling at least one of their position, orientation, shape and volume. Thus, as an example, the anthropomorphic phantom 118 as depicted in FIG. 3 may be a phantom simulating an abdominal section of a human, e.g. of a male. Consequently, as an example, the flexible components 126 may e.g. simulate at least one of a human bladder, a human intestine, a human rectum, a human prostate. Other examples, however, are also feasible. In FIG. 3, for example, a synthetic bladder 128, a synthetic intestine 130, a synthetic rectum 132 and a synthetic prostate 134 are schematically depicted. It shall be noted, however, that the anthropomorphic phantom 118 may also comprise an arbitrary subset of these only one or more of these flexible components 126 and/or one or more further flexible components 126 of other types.

The anthropomorphic phantom 118, specifically at least one of the flexible components 126, may further comprise at least one cavity 136 for receiving at least one dosimeter. In FIG. 3, two such cavities 136 are indicated by circles on the synthetic bladder 128 and the synthetic prostate 134.

The anthropomorphic phantom 118 further comprises at least one receptacle 138 for receiving the flexible components 126. The receptacle 138 may further at least partially be filled with at least one matrix medium, e.g. a gel, such as agarose, which may at least partially surround the flexible components 126. The receptacle 138 is at least partially flexible. As an example, the receptacle 138 may fully or partially be made of a plastic material, such as at least one elastomeric material, e.g. silicone. Other materials or combinations of materials are also feasible. Thus, the receptacle 138 may comprise at least one flexible portion and at least one rigid portion. As indicated in FIG. 3, the receptacle 138 may correspond to the dimensions of an abdominal section and the top of the thighs of a human. Other examples, however, are also feasible.

The anthropomorphic phantom 118 further comprises a plurality of actuators 140 configured for at least one of deforming and moving the flexible components 126 within the receptacle 138. The actuators 140, specifically independently from each other, may be selected from the group consisting of: an electromechanical actuator 142; a piezoelectric actuator 144; a hydraulic actuator 146; a pneumatic actuator 148. The actuators 140, specifically independently from each other, may be selected from the group consisting of: a linear motion actuator 150, specifically a linear motion actuator 150 configured for at least one of pushing and pulling; a rotation actuator. At least one of the actuators 140 may be operatively connected to at least one membrane 154, specifically at least one synthetic membrane 156. The actuator 140 operatively connected to the membrane 154 may be configured for simulating at least one motion of the human body, selected from the group consisting of: a breathing; a swallowing; a coughing; a hiccup. The membrane 154 may comprise a synthetic diaphragm 158. As indicated in FIG. 3, the synthetic diaphragm 158 may be deformed by using the actuators 140. The actuators 140 may push on selective parts of the synthetic diaphragm 158 to deform it. The deformation of the synthetic diaphragm 158 may transfer to the adjacent synthetic bladder 128 and/or the adjacent synthetic intestine 130.

At least one of the flexible components 126 may comprise at least one flexible side wall and a lumen at least partially surrounded by the flexible side wall, wherein at least one of the actuators 140 may be assigned to the flexible component 126 and may be configured for controlling a filling of the lumen with at least one fluidic material. The actuator 140 may be configured for controlling at least one of a pressure of the fluidic material within the lumen and a flow of the fluidic material through the lumen. The test system 124 may be configured for controlling filling of the flexible components 126 simulating an action of one of a human bladder and a human rectum. As indicated in FIG. 3, the synthetic bladder 128 and/or the synthetic rectum 132 may each be filled with a fluidic material by using the actuators 140.

The test system 124 further comprises a control device 122 for controlling the phantom 118. As depicted in FIG. 1 and outlined above, the control device 122 may further be configured for at least partially controlling the imaging device 112 and/or the radiation system 114. Alternatively, the control device 122 may be configured for controlling the phantom 118, only.

As depicted in FIG. 2, the control device 122 comprises a programmable logic controller 160. The programmable logic controller 160 may be configured for superordinate control of a functionality of the phantom 118. The programmable logic controller 160 may be a device according to the DIN/EN IEC 61131 standard and/or the IEC 61131 standard, specifically IEC 61131-3. The programmable logic controller 160 may further comprise at least one feedback loop, specifically a proportional-integral-derivative controller.

The control device 122 further comprises a plurality of controller nodes 162 and a plurality of device controllers 164 configured for controlling the actuators 140. As indicated in FIG. 2, the programmable logic controller 160, the controller nodes 162 and the device controllers 164 may specifically be spatially distributed. Alternatively, the programmable logic controller 160, the controller nodes 162 and the device controllers 164 may be spatially grouped in one assembly.

The control device 122 further comprises at least one real-time bus interface 166 connecting the controller nodes 162 to the programmable logic controller 160 and to the device controllers 164. The real-time bus interface 166 may comprise at least one hard real-time field bus interface, specifically at least one of: field-bus, specifically an Ethernet-based fieldbus; an EtherCAT, a DeviceNet, a Profibus, a Profinet, an Interbus, a Modbus and a SERCOS.

The programmable logic controller 160 is configured to act as a master device with respect to the controller nodes 162, specifically with respect to each of the controller nodes 162. The controller nodes 162 are configured to act as master devices with respect to the device controllers 164. The controller nodes 162, specifically each of the controller nodes 162, may be configured to act as slave devices with respect to the programmable logic controller 160. The device controllers 164, specifically each of the device controllers 164, may be configured to act as slave devices with respect to their corresponding controller nodes 162.

The programmable logic controller 160 may be configured for transferring at least one of the flexible components 126 into at least one target configuration. At least one of the controller nodes 162 may be configured for implementing the target configuration by providing commands to at least one of the device controllers 164. The device controller 164 may be configured for providing at least one command corresponding to the target configuration to at least one of the actuators 140, the actuator 140 being assigned to the flexible component 126. The target configuration may be selected from the group consisting of a static target configuration and a dynamic target configuration. The programmable logic controller 160 may be configured for generating the dynamic target configuration by using at least one algorithm determining a time-development of the target configuration of the flexible component 126. The algorithm determining the time-development of the target configuration may be configured for simulating a motion of the respective flexible component 126, specifically a motion of the flexible component 126 induced by the motion of the part of the human body 116. The test system 124 may be configured for simulating motion of the part of the human body 116 in a velocity range, specifically a velocity range of a velocity of movement of at least one of the flexible components 126, of 0 m/s to 0.20 m/s, specifically of 0 m/s to 0.10 m/s, more specifically of 0 m/s to 0.02 m/s. The control device 122 may comprise at least one sensor-based feedback loop for controlling the transferring of the flexible component 126 into the target configuration.

The phantom 118 may further comprise at least one sensor device 168, wherein the control device 122 is further configured for receiving sensor data from the sensor device 168. The at least one sensor device 168 may be configured for determining at least one item of state information of at least one of the flexible components 126. The item of state information may comprise at least one item selected from the group consisting of: a position of the flexible component 126; an orientation of the flexible component 126; a deformation of the flexible component 126; an acceleration of the flexible component 126; a pressure of the flexible component 126; flow throughput of a liquid through the flexible component 126; a filling level of the flexible component 126. As an example which is indicated in FIG. 3, the synthetic bladder 128, the synthetic intestine 130 and the synthetic rectum 132 may each comprise a sensor device 168 for determining a flow throughput and/or a filling level.

As depicted in FIG. 2, the control device 122 may further comprise at least one sensor device controller 170 configured for controlling the at least one sensor device 168. The control device 122 may further comprise at least one sensor controller node 172. The programmable logic controller 160 may further be configured to act as a master device with respect to the at least one sensor controller node 172. The at least one sensor controller node 172 may be configured to act as a master device with respect to the at least one sensor device controller 170. The at least one real-time bus interface 166 may connect the at least one sensor controller node 172 to the programmable logic controller 160 and to the at least one sensor device controller 170. Additionally or alternatively, at least one of the device controllers 164 may further be configured for controlling the at least one sensor device 168. Thus, at least one of the sensor device controllers 170 may be embodied as a separate component and/or may fully or partially be physically integrated in at least one of the device controllers 164. Further, at least one of the sensor controller nodes 172 may be embodied as a separate component and/or may fully or partially be physically integrated in at least one of the controller nodes 162.

The test system 124 may further comprise at least one radiation shielding 174 for separating a treatment room 176 from an environment. At least the programmable logic controller 160 may be placed in the environment outside the treatment room 176. Further, at least one of the following components may be placed outside the treatment room 176: at least a part of the controller nodes 162; at least a part of the actuators 140; at least a part of the device controllers 164. As an example which is depicted in FIG. 2, all actuators 140 and device controllers 164 may be placed inside the treatment room 176 and all controller nodes 162 may be placed outside the treatment room 176. At least a part of the real-time bus interface 166 may go around and/or go through the radiation shielding 174. The actuators 140 may be configured for use in magnetic resonance environments 178. As further depicted in FIG. 2, also all sensor devices 168 and sensor device controllers 170 may be placed inside the treatment room 176 and all sensor controller nodes 172 may be placed outside the treatment room 176. The sensor devices 168 may be configured for use in magnetic resonance environments 178. As said, at least one of the sensor device controllers 170 may be embodied as a separate component and/or may fully or partially be physically integrated in at least one of the device controllers 164 and at least one of the sensor controller nodes 172 may be embodied as a separate component and/or may fully or partially be physically integrated in at least one of the controller nodes 162. Generally, one or more of the sensor device controllers 170, the device controllers 164, the sensor controller nodes 172 and the controller nodes 162 may be embodied as a separate component and/or may fully or partially be physically integrated in one device, wherein the device may be placed outside the treatment room 176.

The control device 122 may further comprise a system clock 179. The system clock 179 may fully or partially be embodied by software and/or by hardware. The system clock may be or may be provided by an element such as a port of a component, such as a port of a processor chip and/or another type of integrated circuit. The system clock may be configured to generate or provide at least one system clock signal, which often is identified with the "system clock". Thus, when referring to the "system clock", either the element or the signal or both may be comprised. The programmable logic controller 160 may be configured to communicate with the controller nodes 162 in predefined time intervals defined by the system clock 179. The programmable logic controller 160 may act as a system clock 179 and/or may be configured for generating and distributing a system clock signal. The controller nodes 162 may be configured to communicate with the device controllers 164 in predefined time intervals defined by the system clock 179. The predefined time intervals may have a length of 0.1 Milliseconds to 100 Milliseconds, specifically 1 Millisecond to 10 Milliseconds, more specifically 1 Millisecond. The control device may be configured for executing a real-time protocol, wherein an exchange of a command between the programmable logic controller 160 and the controller nodes 162 and an exchange of a command between at least one of the controller nodes 162 and at least one of the device controllers 164 takes place within one predefined time interval. A cycle rate of the control device may be 0.5 kHz to 20 kHz, specifically 1 kHz to 8 kHz.

Figure 4:
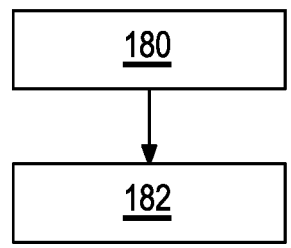
FIG. 4 shows a flow chart of an embodiment of a method of simulating motion of at least one part of a human body.

FIG. 4 shows a flow chart of an embodiment of a method of simulating motion of at least one part of a human body 116. The method of simulating motion of the part of the human body 116 comprises the following method steps:
i. (denoted by reference sign 180) providing at least one test system 124 as described herein, e.g. according to any one of the embodiments disclosed above and/or according to any one the embodiments disclosed in further detail below;
ii. (denoted by reference sign 182) transferring, by using the programmable logic controller 122, at least one of the flexible components 126 into at least one target configuration, wherein at least one of the controller nodes 162 implements the target configuration by providing commands to at least one of the device controllers 164, wherein the device controller 162 provides at least one command corresponding to the target configuration to at least one of the actuators 140, the actuator 140 being assigned to the flexible component 126.

At least step ii. may be computer-controlled. Further, one or more of the method steps may be performed once or repeatedly. The method may comprise further method steps which are not listed.

Figure 5:
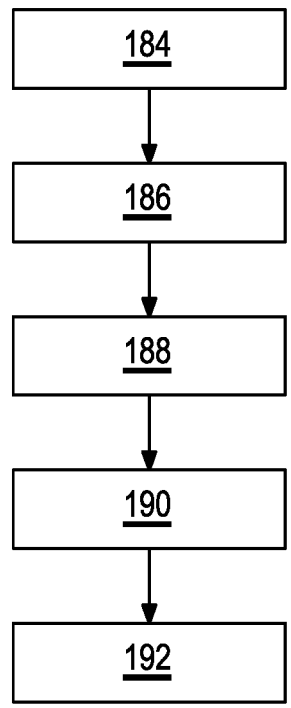
FIG. 5 shows a flow chart of an embodiment of a method of testing a system for radiologic treatment.

FIG. 5 shows a flow chart of an embodiment of a method of testing a system 110 for radiologic treatment. The method of testing a system 110 for radiologic treatment comprises the following method steps:
I. (denoted by reference sign 184) providing at least one test system 124 according to any one of the embodiments disclosed above referring to a test system 124;
II. (denoted by reference sign 186) placing the phantom 118 of the test system 124 into at least one treatment position of the system for radiologic treatment;
III. (denoted by reference sign 188) imaging at least one part of the phantom 118 by using the imaging device 112 of the system 110 for radiologic treatment;
IV. (denoted by reference sign 190) simulating motion of at least one part of a human body 116 by using the method according to any one of the embodiments disclosed above referring to a method of simulating motion of at least one part of a human body 116;
V. (denoted by reference sign 192) evaluating a system response of the system 110 for radiologic treatment to the simulated motion.

The method steps may be performed in the given order. It shall be noted, however, that a different order is also possible. Further, one or more of the method steps may be performed once or repeatedly. Further, two or more of the method steps may be performed simultaneously or in a timely overlapping fashion. The method may comprise further method steps which are not listed.

The evaluation of the system response in step V. may comprise evaluating if the controlling of the irradiation in accordance with the at least one item of information on the spatial configuration of the part of the human body 116 comprises recognizing a re-configuration due to the motion simulated in step IV. The evaluation of the system response in step V. may further comprise adjusting may further comprise adjusting the irradiation in accordance with the recognized re-configuration, specifically by at least one of adjusting a spatial configuration of the irradiation, adjusting an orientation of the irradiation and adjusting a shape of the irradiation. The irradiation may be paused during the adjusting. The method may further comprise providing information on the evaluating in step V., specifically by providing an evaluation report. At least steps III. to V. may be computer-controlled.

LIST OF REFERENCE NUMBERS 110 system for radiologic treatment
112 imaging device
114 radiation system
116 part of a human body
118 anthropomorphic phantom
120 bed
122 control device
124 test system for testing the system for radiologic treatment
126 flexible component
128 synthetic bladder
130 synthetic intestine
132 synthetic rectum
134 synthetic prostate
136 cavity
138 receptacle
140 actuator
142 electromechanical actuator
144 piezoelectric actuator
146 hydraulic actuator
148 pneumatic actuator
150 linear motion actuator
154 membrane
156 synthetic membrane
158 synthetic diaphragm
160 programmable logic controller
162 controller nodes
164 device controller
166 real-time bus interface
168 sensor device
170 sensor device controller
172 sensor controller node
174 radiation shielding
176 treatment room
178 magnetic resonance environments
179 system clock
180 method step i.
182 method step ii.
184 method step I.
186 method step II.
188 method step III.
190 method step IV.
192 method step V.

The invention claimed is:
1. A test system for testing a system for radiologic treatment, comprising
(A.) at least one anthropomorphic phantom for simulating motion of at least one part of a human body, the phantom comprising
a plurality of flexible components, each flexible component simulating at least a part of a human organ,
a receptacle for receiving the flexible components, the receptacle being at least partially flexible, and
a plurality of actuators configured for at least one of deforming and moving the flexible components within the receptacle; and
(B.) a control device; for controlling the phantom, comprising
a programmable logic controller,
a plurality of controller nodes, a plurality of device controllers configured for controlling the actuators, and at least one real-time bus interface connecting the controller nodes to the programmable logic controller and to the device controllers, wherein the programmable logic controller is configured to act as a master device with respect to the controller nodes, wherein the controller nodes are configured to act as master devices with respect to the device controllers.

2. The test system according to claim 1, wherein the phantom further comprises at least one sensor device, wherein the control device is further configured for receiving sensor data from the sensor device, wherein the at least one sensor device is configured for determining at least one item of state information of at least one of the flexible components.

3. The test system according to claim 2, wherein the item of state information comprises at least one item selected from the group consisting of: a position of the flexible component; an orientation of the flexible component; a deformation of the flexible component; an acceleration of the flexible component; a pressure of the flexible component; flow throughput of a liquid through the flexible component; a filling level of the flexible component.

4. The test system according to claim 2, wherein at least one of the device controllers is further configured for controlling the at least one sensor device.

5. The test system according to claim 2, wherein the control device further comprises at least one sensor device controller configured for controlling the at least one sensor device, wherein the control device further comprises at least one sensor controller node, wherein the programmable logic controller is further configured to act as a master device with respect to the at least one sensor controller node, wherein the at least one sensor controller node is configured to act as a master device with respect to the at least one sensor device controller, wherein the at least one real-time bus interface connects the at least one sensor controller node to the programmable logic controller and to the at least one sensor device controller.

6. The test system according to claim 1, wherein the programmable logic controller is configured for transferring at least one of the flexible components into at least one target configuration, wherein at least one of the controller nodes is configured for implementing the target configuration by providing commands to at least one of the device controllers, wherein the device controller is configured for providing at least one command corresponding to the target configuration to at least one of the actuators, the actuator being assigned to the flexible component.

7. The test system according to claim 6, wherein the target configuration is a dynamic target configuration, wherein the programmable logic controller is configured for generating the dynamic target configuration by using at least one algorithm determining a time-development of the target configuration of the flexible component.

8. The test system according to claim 7, wherein the algorithm determining the time-development of the target configuration is configured for simulating a motion of the respective flexible component.

9. The test system according to claim 6, wherein the control device comprises at least one sensor-based feedback loop for controlling the transferring of the flexible component into the target configuration.

10. The test system according to claim 1, wherein the actuators are selected from the group consisting of: an electromechanical actuator; a piezoelectric actuator; a hydraulic actuator; a pneumatic actuator.

11. The test system according to claim 1, wherein at least one of the flexible components comprises at least one flexible side wall and a lumen at least partially surrounded by the flexible side wall, wherein at least one of the actuators is assigned to the flexible component and is configured for controlling a filling of the lumen with at least one fluidic material.

12. The test system according to claim 1, wherein the control device further comprises a system clock, wherein the programmable logic controller is configured to communicate with the controller nodes and wherein the controller nodes are configured to communicate with the device controllers in predefined time intervals defined by the system clock, wherein the control device is configured for executing a real-time protocol, wherein an exchange of a command between the programmable logic controller; and the controller nodes and an exchange of a command between at least one of the controller and at least one of the device controllers takes place within one predefined time interval.

13. A method of simulating motion of at least one part of a human body, the method comprising:
(i.) providing at least one test system claim 1;
(ii.) transferring, by using the programmable logic controller into at least one target configuration, wherein at least one of the controller nodes implements the target configuration by providing commands to at least one of the device controllers, wherein the device controller provides at least one command corresponding to the target configuration to at least one of the actuators, the actuator being assigned to the flexible component.

14. A method of testing a system for radiologic treatment, the system comprising at least one imaging device for imaging at least one part of a human body and at least one radiation system for irradiating the part of the human body with ionizing radiation, the system being configured for controlling the irradiation in accordance with at least one item of information on a spatial configuration of the part of the human body, the method comprising:
(I.) providing at least one test system according claim 1;
(II.) placing the phantom of the test system into at least one treatment position of the system for radiologic treatment;
(III.) imaging at least one part of the phantom by using the imaging device of the system for radiologic treatment;
(IV.) simulating motion of at least one part of a human body by using the method according to the preceding claim;
(V.) evaluating a system response of the system for radiologic treatment to the simulated motion.

15. The method according to claim 14, wherein the evaluation of the system response in step (V.) comprises evaluating if the controlling of the irradiation in accordance with the at least one item of information on the spatial configuration of the part of the human body comprises recognizing a re-configuration due to the motion simulated in step (IV.) and further comprises adjusting the irradiation in accordance with the recognized re-configuration.

* * * * *